(12) United States Patent
Sotzing

(10) Patent No.: US 9,944,757 B2
(45) Date of Patent: Apr. 17, 2018

(54) ELECTROCHROMIC COPOLYMERS FROM PRECURSORS, METHOD OF MAKING, AND USE THEREOF

(71) Applicant: THE UNIVERSITY OF CONNECTICUT, Farmington, CT (US)

(72) Inventor: Gregory Allen Sotzing, Mansfield Center, CT (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 179 days.

(21) Appl. No.: 14/416,503

(22) PCT Filed: Jul. 23, 2013

(86) PCT No.: PCT/US2013/051558
§ 371 (c)(1),
(2) Date: Jan. 22, 2015

(87) PCT Pub. No.: WO2014/018472
PCT Pub. Date: Jan. 30, 2014

(65) Prior Publication Data
US 2015/0232622 A1 Aug. 20, 2015

Related U.S. Application Data

(60) Provisional application No. 61/674,477, filed on Jul. 23, 2012.

(51) Int. Cl.
*H01B 1/12* (2006.01)
*C08G 75/06* (2006.01)
(Continued)

(52) U.S. Cl.
CPC ............ *C08G 75/06* (2013.01); *B05D 5/06* (2013.01); *C09D 5/24* (2013.01); *C09D 181/02* (2013.01); *H01B 1/124* (2013.01)

(58) Field of Classification Search
CPC .. C08G 61/122; C08G 61/123; C08G 61/126; C08G 77/52; C08G 77/60; C08G 79/00; H01L 51/0094; H01B 1/124
See application file for complete search history.

(56) References Cited

U.S. PATENT DOCUMENTS 5,066,111 A 11/1991 Singleton et al.
5,111,327 A 5/1992 Blohm et al.
(Continued)

FOREIGN PATENT DOCUMENTS

DE 10036954 2/2002
EP 0577406 A1 5/1994
(Continued)

OTHER PUBLICATIONS

"Device with ionic liquid electrolyte." Electronic Supplementary Material (ESI) for Journal of Materials Chemistry; The Royal Society of Chemistry, 2011. 3 pages.
(Continued)

*Primary Examiner* — Mark Kopec
*Assistant Examiner* — Jaison P Thomas
(74) *Attorney, Agent, or Firm* — Cantor Colburn LLP

(57) ABSTRACT

This invention relates to electrochromic copolymers having a specific color transition prepared from precursors containing Si, Ge, Sn, or Pb, methods of producing such copolymers and precursors, and applications utilizing the copolymers to prepare electrochromic devices.

26 Claims, 10 Drawing Sheets

(51) Int. Cl.
 *C09D 5/24* (2006.01)
 *C09D 181/02* (2006.01)
 *B05D 5/06* (2006.01)

(56) References Cited

U.S. PATENT DOCUMENTS

| | | | |
|---|---|---|---|
| 5,253,100 | A | 10/1993 | Yang et al. |
| 5,377,037 | A | 12/1994 | Branz et al. |
| 5,608,567 | A | 3/1997 | Grupp |
| 5,729,379 | A | 3/1998 | Allemand et al. |
| 6,157,479 | A | 12/2000 | Heuer et al. |
| 6,330,101 | B1 | 12/2001 | Yamamoto et al. |
| 6,368,363 | B1 | 4/2002 | Kobatake et al. |
| 6,433,913 | B1 | 8/2002 | Bauer et al. |
| 6,482,299 | B1 | 11/2002 | Inganas et al. |
| 6,635,729 | B1 | 10/2003 | Groenendaal et al. |
| 6,791,738 | B2 | 9/2004 | Reynolds et al. |
| 6,995,223 | B2 | 2/2006 | Groenendaal et al. |
| 7,321,012 | B2 | 1/2008 | Sotzing |
| 7,411,716 | B2 | 8/2008 | Oh et al. |
| 7,586,663 | B1 | 9/2009 | Radmard et al. |
| 7,626,748 | B2 | 12/2009 | Radmard et al. |
| 7,630,117 | B2 | 12/2009 | Oh et al. |
| 7,737,247 | B2 | 6/2010 | Sotzing |
| 7,808,692 | B2 | 10/2010 | Karmhag et al. |
| 7,874,666 | B2 | 1/2011 | Xu et al. |
| 7,951,902 | B2 | 5/2011 | Sotzing |
| 7,952,785 | B2 | 5/2011 | Karmhag et al. |
| 8,227,567 | B2 * | 7/2012 | Sotzing ............... C08G 61/122 525/328.5 |
| 8,404,515 | B2 | 3/2013 | Sotzing |
| 8,513,377 | B2 | 8/2013 | Sotzing et al. |
| 8,890,130 | B2 | 11/2014 | Sotzing et al. |
| 9,127,121 | B2 * | 9/2015 | Sotzing ............... C08G 61/122 |
| 2002/0149739 | A1 | 10/2002 | Perrott et al. |
| 2002/0171907 | A1 | 11/2002 | Vincent et al. |
| 2003/0087533 | A1 | 5/2003 | Stupp et al. |
| 2003/0232195 | A1 | 12/2003 | Reneker et al. |
| 2004/0072987 | A1 | 4/2004 | Groenendaal et al. |
| 2004/0242792 | A1 | 12/2004 | Sotzing |
| 2005/0157369 | A1 | 7/2005 | Xu et al. |
| 2005/0246888 | A1 | 11/2005 | Reynolds et al. |
| 2006/0047030 | A1 | 3/2006 | Yoshida et al. |
| 2006/0262377 | A1 | 11/2006 | Kojima |
| 2007/0008603 | A1 | 1/2007 | Sotzing et al. |
| 2007/0089845 | A1 | 4/2007 | Sotzing et al. |
| 2007/0191576 | A1 * | 8/2007 | Sotzing ............... C08G 61/122 528/176 |
| 2008/0291522 | A1 | 11/2008 | Varaprasad et al. |
| 2009/0203873 | A1 | 8/2009 | Sotzing |
| 2010/0113727 | A1 | 5/2010 | Sotzing |
| 2010/0245971 | A1 | 9/2010 | Sotzing et al. |
| 2010/0283040 | A1 | 11/2010 | Bendikov et al. |
| 2011/0043886 | A1 | 2/2011 | Jeon et al. |
| 2011/0201826 | A1 | 8/2011 | Sotzing |
| 2011/0233532 | A1 | 9/2011 | Sotzing et al. |
| 2011/0251370 | A1 * | 10/2011 | Beaujuge ............ C08G 61/126 528/9 |
| 2011/0288253 | A1 * | 11/2011 | Reynolds ............ C08G 61/122 526/240 |
| 2013/0161600 | A1 | 6/2013 | Sotzing et al. |
| 2013/0235323 | A1 | 9/2013 | Sotzing et al. |
| 2015/0331293 | A1 | 11/2015 | Sotzing et al. |
| 2016/0056382 | A1 | 2/2016 | Sotzing et al. |
| 2016/0244553 | A1 * | 8/2016 | Reynolds ............ C08G 61/123 |

FOREIGN PATENT DOCUMENTS

| | | |
|---|---|---|
| EP | 1760110 A1 | 3/2007 |
| EP | 1928000 A1 | 6/2008 |
| EP | 2196847 A1 | 6/2010 |
| EP | 2049944 B1 | 6/2011 |
| EP | 2336255 A1 | 6/2011 |
| JP | 61252535 A | 11/1986 |
| JP | S63128034 A | 5/1988 |
| JP | 63225688 A | 9/1988 |
| JP | 3132724 A | 6/1991 |
| JP | 2007041579 | 2/2007 |
| JP | 2007163865 | 6/2007 |
| KR | 2007007131 | 7/2007 |
| WO | 03046106 A1 | 6/2003 |
| WO | 03054052 A1 | 7/2003 |
| WO | 03054053 A1 | 7/2003 |
| WO | 2004031192 A1 | 4/2004 |
| WO | 2006117800 A2 | 11/2006 |
| WO | 2007008977 A1 | 1/2007 |
| WO | 2007066353 A2 | 6/2007 |
| WO | 2008013499 A1 | 1/2008 |
| WO | 2008118967 A1 | 10/2008 |
| WO | 2009031422 A1 | 3/2009 |
| WO | 2009117025 A1 | 9/2009 |
| WO | 2009124850 A1 | 10/2009 |
| WO | 2011119664 A2 | 9/2011 |
| WO | 2014018472 A1 | 1/2014 |

OTHER PUBLICATIONS

Agrun, A. "Patterning of Conjugated Polymers for Electrochromic Devices" A Dissertation Presented to The Graduate School of the University of Florida, University of Florida, 2004, 167 pages.

Aubert et al. "Microporous Patterned Electrodes for Color-Matched Electrochromic Polymer Displays" American Chemical Society, 2004, 8 pages.

Beaujuge et al. "The donor-acceptor approach allows a black-to-transmissive switching polymeric electrochrome" Nature Materials, vol. 7, Oct. 2008, 5 pages.

Beaujuge et al., Spray Processable Green to Highly Transmissive Electrochromics via Chemically Polymerizable Donor-Acceptor Heterocyclic Pentamers, Adv. Mater., 2008, 20, 2772-2776.

Bokria et al. "Solid-State Conversion of Processable 3,4-Ethylenedioxythiphene (EDOT) Containing Poly(arylsilane) Precursors to π-Conjugated Conducting Polymers" Advanced Materials 2008, 20, pp. 1775-1778.

Campos et al., "Photovoltaic activity of a PolyProDOT derivative in a bulk heterojunction solar cell", Solar Energy Materials & Solar Cells 90, 2006, pp. 3531-3546.

Coffey et a., "A Facile Synthesis of 3,4-Dialkoxythiophenes", Synthetic Communications, 26(11), 1996, pp. 2205-2212.

D'angelo et al. "Chemical stability of conducting polymers: FriedeleCrafts reactions of alcohols with poly(3,4-ethylenedioxythiophene) (PEDOT)" Polymer 48 (2007) 4328e4336.

Ding et al., "A simple, low waste and versatile procedure to make polymer electrocheromic devices." Journal of Materials Chemistry; 2011, 21, pp. 11873-11878.

Ding, Spring 2011 MRS meeting slides A Simple Low-waste and Versatile Procedure for Polymer Electrochromic Devices and Displays, MRS_spring_2011—no video, 21 slides.

Ding; "In situ Polymerization of Conjugated Polymers and All-Organic Electrochromic Fabrics"; University of Connecticut; 2011; 240 pages.

Duluard et al.; "Electrochromic devices based on in situ polymerised EDOT and Prussian Blue: influence of transparent conductin oxide and electrolyte composition-towards up-scalling"; New J. Chem, 2011, 35; pp. 2314-2321.

Galand et al., "Spray Processable Hybrid 3,4-Propylenedioxythionphene: Phenylene Electrochromic Polymers", Macromolecules 39, 2006, pp. 7286-7294.

Gaupp et al., "Composite Coloration Efficiency Measurements of Electrochromic Polymers Based on 3,4-Alkylenedioxythiophenes", Chem. Mater. 14, 2002, pp. 3694-3970.

Gaupp et al., "Poly(ProDOT-Et2): A High-Contrast, High-Coloration Efficiency Electrochromic Polymer", Macromol. Rapid. Commun. 23, 2002, pp. 885-889.

Heywang et al., "Poly(alkylenedioxythiophene)s- New, Very Stable Conducting Polymers", Advanced Materials, 4(2), 1992, pp. 116-118.

(56) References Cited

OTHER PUBLICATIONS

Hwang, J., Tanner, D. B. "Optical properties of nondegenerate ground-state polymers: Three Dioxythiophene-based conjugated polymers" The American Physical Society, 2003, 10 pages.
Icli et al. "A new soluble neutral state black electrochromic copolymer via a donor-acceptor approach" Organic Electronics 11 (2010) 1255-1260.
International Search Report; International Application No. PCT/US2013/051558; International Filing Date Jul. 23, 2013; 6 pages.
Invernale et al. "Variable-color poly(3,4-propylenedioxythiophene) electrochromics from precursor polymers" Published by Elsevier Ltd., Polymer 51 (2010) 378-382, available online Dec. 21, 2009.
Invernale et al., "Polythieno[3,4-b]thiophene as an Optically Transparent Ion-Storage Layer", Chemistry of Materials, 21, 2009, pp. 3332-3336.
Invernale et al., "Preparation of Conjugated Polymers Inside Assembled Solid-state Devices", Advanced Materials 22, 2010, pp. 1379-1382.
Krishnamoorthy et al.; "Rational design of an electrochromic polymer with high contrast in the visible region: dibenzyl substituted poly (3,4-propylenedioxythiophehe)"; Journal of Chemistry; 2001; pp. 2909-2911.
Kumar Anil et al.; "Conducting Poly(3-4-alkylenedioxythiophene) Derivatives as Fast Electrochromics with High-Contrast Ratios"; Chem Mater.; 1998, 10, pp. 896-902.
Lee, K. Sotzing, G. "New Method to Prepare Conjugated Polymers; Polyarylsiloxane as Precursors to Conjugated Polymers" Polymeric Materials: Science & Engineering 2010, 103, 128, 3 pages.
Lee, K. Sotzing, G. "Preparation of Conjugated Polymers from Polyarylsiloxnae Precursors" Abstract #1307, 219th ECS Meeting, © 2011 The Electrochemical Society, 2 pages.
Li, et al., "Nanofibers of Conjugated Polymers Prepared by Electrospinning With A Two-Capillary Spinneret", Adv. Mater. Nov. 18, 2004, 16, No. 22, pp. 2062-2066.
Ozkut et al., "A blue to highly transmissive soluble electrochromic polymer based on poly (3,4-propylenedioxyselenophene) with a high stability and coloration efficiency", Journal of Materials Chemsitry, 21, 2011, pp. 5268-5272.
Padilla et al., "Electrochemical study of dual conjugated polymer electrochromic devices", Journal of Electroanalytical Chemistry 609, 2007, pp. 75-84.
Padilla et al., "High contrast solid-state electrochromic devices frmo substituted 3,4-propylenedioxythiophenes using the dual conjugated polymer approach", Synthetic Metals 157, 2007, pp. 261-268.
Reeves et al., "Dual Cathodically and Anodically Coloring Electrochromic Polymer Based on a Spiro Bipropylenedioxythionphene [(Poly(spiroBiProDOT)]", Advanced Materials, 14(10), 2002, pp. 717-719.
Sapp et al., "High Contrast Ratio and Fast-Switching Dual polymer Electrochromic Devices", Chem. Mater. 10, 1998, pp. 2101-2108.
Sapp et al., "Rapid Switching Solid State Electrochromic Devices Based on Complementary Conducting Polymer Films", Adv. Material, 8, No. 10, pp. 808-811.
Seshadri et al., "Optimization, preparation, and electrical short evaluation for 30 cm2 active area dual conjugated polymer electrochromic windows", Organic Eelctronics 8, 2007, pp. 367-381.
Sotzing webpage "Electrochromic Devices"; Institute of Materials Sciences; University of Connecticut; downloaded from http://www.ims.uconn.edu/~sotzing_grp/research/ECDevices.html; on May 31, 2011; 2 pages.
Sotzing, et al, "Oxidative Sold-State Crosslinking of Polymer Precursors to Pattern Intrinsically Conducting Polymers", Polymeric Materials: Science & Engineering 2002, 87, 371-87, 372.
Sotzing, et al., "Electrochromic Spandex and Other Fabrics for Adaptive Camouflage", MRS Apr. 2011.
Thompson et al., "Soluble Narrow Band Gap and Blue Propylenedioxythiophene-Cyanovinylene Polymers as Multifunctional Materials for Photovoltaic and Electrochromic Applications", J. Am. Chem. Soc. 128, 2006, pp. 12714-12725.
U.S. Appl. No. 10/978,834, filed Nov. 1, 2004; 28 pages.
Walczak et al., "Easily Oxidized high Band Gap Conjugated Polymers", Polymer Preprints 45(1), 2004, p. 229.
Welsh Dean M. et al.; "Enhanced Contrast Ratios and Rapid Wwitching in Electrochromics Based on Poly(3,4-propylemedioxythiophene) Derivatives"; Advanced Materials; 1999, II, No. 16; pp. 1379-1382.
Written Opinion of the International Searching Authority; International Applciation No. PCT/US2013/051558; International Filing Date Jul. 23, 2013; 7 pages.
Zong et al., 3,4-Alkylenedioxy ring formation via double Mitsunobu reactions: an efficient route for the synthesis of 3,4-ethylenedioxythiophene (EDOT) and 3,4-propylenedioxythiophene (ProDOT) derivatives as monomers for electron-rich conducting polymer.

* cited by examiner

ELECTROCHROMIC COPOLYMERS FROM PRECURSORS, METHOD OF MAKING, AND USE THEREOF

TECHNICAL FIELD

This invention relates to electrochromic copolymers having a specific color transition prepared from precursors containing Si, Ge, Sn, or Pb; methods of producing such copolymers and precursors; and applications utilizing the precursors or copolymers to prepare electrochromic devices.

BACKGROUND

The color switching accompanied with external bias is defined as electrochromism, where the external bias triggers either a change of molecular stack or electron transfer (redox process). Since a conjugated polymer offers the tool to tune the optical properties by structural modification, polymer electrochromics have been studied intensively. Further, a conjugated polymer which changes its color by a redox process, has high optical contrast ratio, rapid redox switching, and long-term stability have made the polymer a desired material for various electrochromic device applications.

Although various colors of the conjugated polymer at the neutral state have been shown, including colors such as blue, green, yellow, and red, only a few examples of black electrochromic polymers have been reported to date. This is due to the complexity of designing materials absorbing the entire visible region (about 390-750 nm) evenly. The donor-acceptor approach offers a low band gap polymer, which covers most of the visible region. The two distinct absorption bands, generally shown in a donor-acceptor type polymer, are adjustable by the composition of donor and acceptor unit in the polymer backbone. To absorb evenly in the visible region, randomness of the donor and acceptor distribution is needed.

The first black electrochromic polymer was prepared by using a 3,4-propylenedioxythiophene ("ProDOT") derivative as donor and a 2,1,3-benzothiadiazole ("BTD") derivative as acceptor. The random copolymer consisted of donor and acceptor units that were chemically polymerized to yield the polymer. The copolymer showed different absorption spectra varied by the choice of polymerization method, such as FeCl$_3$ mediated polymerization or Pd-catalyzed cross coupling, and the scale of the reaction. However, the composition and randomness of ProDOT and BTD in the conjugated polymer is unchangeable, since the two aromatics are chemically bonded.

The second approach is the electrochemical polymerization of two donor-acceptor types of monomers, one covering blue and red, and the other covering green in the visible region. The resulting conjugated polymer exhibits successful color transition from black to grey, but the method holds the complexity of control of the composition via electrochemical copolymerization and the difficulty to achieve mass production.

There remains a need in the art for improved methods, in terms of convenience and efficiency, to prepare a series of black electrochromic polymers.

BRIEF SUMMARY

In an embodiment, a precursor mixture comprises two precursors, wherein a first precursor is

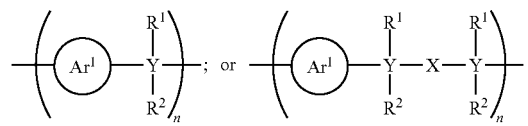

wherein Ar$^1$ is a heteroaryl electron donor unit; each occurrence of R$^1$ and R$^2$ is independently C$_1$-C$_{12}$ alkyl, C$_1$-C$_{12}$ haloalkyl, or aryl; X is O, S, (YR$^1$R$^2$)$_x$, or (CR$^a$R$^b$)$_x$ wherein x is 0, 1, 2, 3, or 4, and R$^a$ and R$^b$ are independently hydrogen, C$_1$-C$_{12}$ alkyl, or C$_1$-C$_{12}$ haloalkyl; each occurrence of Y is independently Si, Ge, Sn, or Pb; and n is about 10 or greater; and wherein a second precursor is

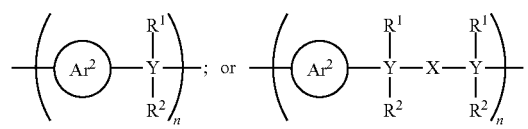

wherein Ar$^2$ is a heteroaryl electron acceptor unit; each occurrence of R$^1$ and R$^2$ is independently C$_1$-C$_{12}$ alkyl, C$_1$-C$_{12}$ haloalkyl, or aryl; X is O, S, (YR$^1$R$^2$)$_x$, or (CR$^a$R$^b$)$_x$ wherein x is 0, 1, 2, 3, or 4, and R$^a$ and R$^b$ are independently hydrogen, C$_1$-C$_{12}$ alkyl, or C$_1$-C$_{12}$ haloalkyl; each occurrence of Y is independently Si, Ge, Sn, or Pb; and n is about 10 or greater.

In an embodiment, a conjugated copolymer comprises a copolymer prepared by converting a precursor mixture comprising two precursors to the conjugated copolymer, wherein the first precursor is

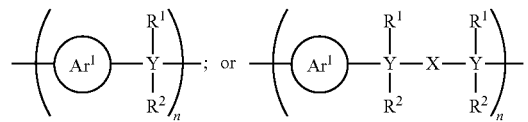

wherein Ar$^1$ is a heteroaryl electron donor unit; each occurrence of R$^1$ and R$^2$ is independently C$_1$-C$_{12}$ alkyl, C$_1$-C$_{12}$ haloalkyl, or aryl; X is O, S, (YR$^1$R$^2$)$_x$, or (CR$^a$R$^b$)$_x$ wherein x is 0, 1, 2, 3, or 4, and R$^a$ and R$^b$ are independently hydrogen, C$_1$-C$_{12}$ alkyl, or C$_1$-C$_{12}$ haloalkyl; each occurrence of Y is independently Si, Ge, Sn, or Pb; and n is about 10 or greater; and wherein the second precursor is

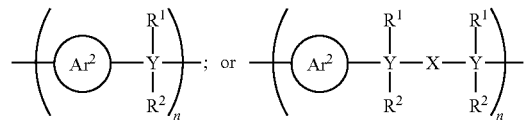

wherein Ar$^2$ is a heteroaryl electron acceptor unit; each occurrence of R$^1$ and R$^2$ is independently C$_1$-C$_{12}$ alkyl, C$_1$-C$_{12}$ haloalkyl, or aryl; X is O, S, (YR$^1$R$^2$)$_x$, or (CR$^a$R$^b$)$_x$ wherein x is 0, 1, 2, 3, or 4, and R$^a$ and R$^b$ are independently hydrogen, C$_1$-C$_{12}$ alkyl, or C$_1$-C$_{12}$ haloalkyl; each occurrence of Y is independently Si, Ge, Sn, or Pb; and n is about 10 or greater, wherein the conjugated copolymer comprises a unit of YR$^1$R$^2$.

In an embodiment, a method of preparing a conductive conjugated copolymer, comprises converting a precursor mixture comprising two precursors to the conductive conjugated copolymer,
wherein a first precursor is

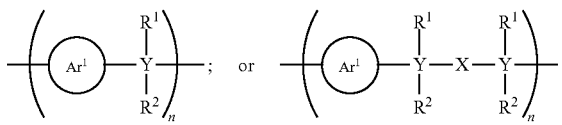

wherein $Ar^1$ is a heteroaryl electron donor unit; each occurrence of $R^1$ and $R^2$ is independently $C_1$-$C_{12}$ alkyl, $C_1$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_{12}$ haloalkyl; each occurrence of Y is independently Si, Ge, Sn, or Pb; and n is about 10 or greater; and
wherein a second precursor is

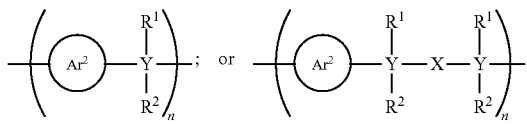

wherein $Ar^2$ is a heteroaryl electron acceptor unit; each occurrence of $R^1$ and $R^2$ is independently $C_1$-$C_{12}$ alkyl, $C_1$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_{12}$ haloalkyl; each occurrence of Y is independently Si, Ge, Sn, or Pb; and n is about 10 or greater, wherein the conjugated copolymer comprises a unit of $YR^1R^2$.

Other embodiments include methods of processing the precursors and articles prepared therefrom.

DETAILED DESCRIPTION

Figure 1A:
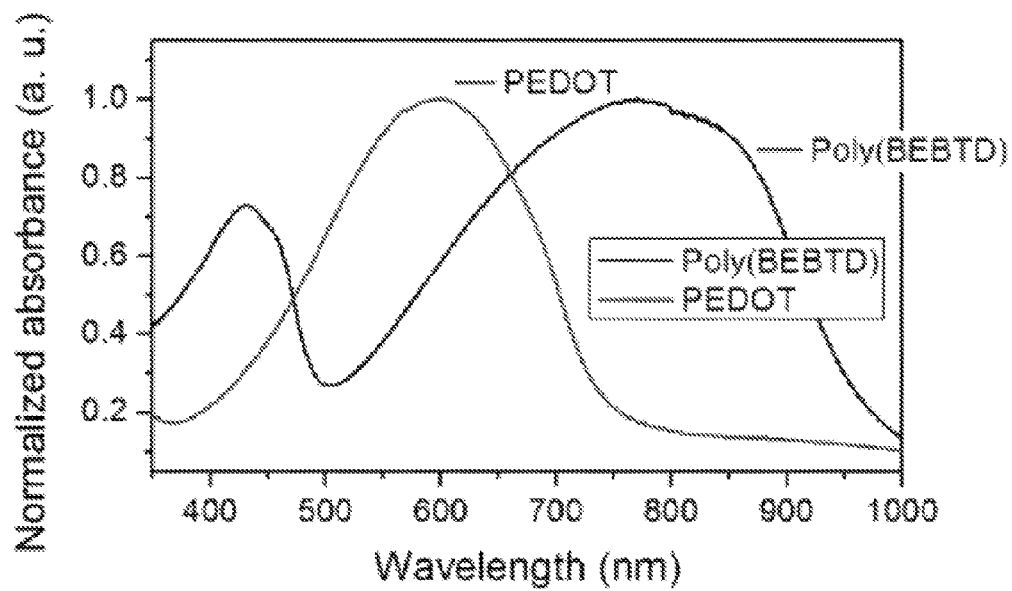
FIG. 1a illustrates the UV-vis-NIR spectra of PEDOT and poly(BEBTD).

Disclosed herein is a method of preparing a conjugated copolymer from precursors (e.g. silane and siloxane precursors, and Ge, Sn, and Pb analogs) by oxidative conversion in the solid state using the donor-acceptor approach to result in a black electrochromic or other electrochromic with a select color. As the precursors are soluble in common organic solvents, multiple numbers of precursors can easily be mixed to form a blend. Further, the composition of donor to acceptor is easily controlled by the change of the ratio of donor-containing precursors to acceptor-containing precursors. Since the blend of precursors is converted to a conjugated copolymer at the final step, the convenient modification of the composition of the pre-mixed blend is possible.

The donor-acceptor type π-conjugated polymer exhibits dual band absorption, varying by the contribution of electron rich and deficient effect of donor and acceptor in the backbone. As used herein "donor" means electron donating and "acceptor" means electron accepting. It offers the tool to modify the saturation or hue of the color of conjugated polymer. Generally, as a number of donor increases in the donor-acceptor conjugated system, the optical properties changes from the spectrum of poly(donor-acceptor-donor) (polyDAD) to that of poly(donor) (polyD). Therefore complementary absorption of polyDAD and polyD in visible region allows for an even absorption in visible region.

Herein is described a method for mixing two or more precursors to form a donor-acceptor composition to precisely tune the color of black generated in the colored state of the resulting electrochromic copolymer. A specific black color is achieved in the dark state by controlling the ratio of the two precursors and by oxidatively converting them to conductive copolymers. The color of the oxidized state of the device remains the same, independent of the different black color achieved by the different compositions. Black is a much desired neutral color for electrochromic devices, especially in applications such as windows, printing, eyewear and camera filters.

As used herein "precursor mixture", "precursor blend", "mixture of precursors" and "blend of precursors" have the same meaning.

It was determined that the blend of precursors are compatible and do not phase separate below the optical resolution, a property needed for the generation of a copolymer electrochromic exhibiting a black color in the colored state of a device.

In one embodiment, a black electrochromic copolymer is prepared from a blend of a BEDOT-containing siloxane precursor as the donor and a BEBTD-containing siloxane precursor as the acceptor.

Disclosed herein are precursor mixtures wherein the precursor contains units of heteroaryls linked by one or more Silicon (Si) containing groups, Germanium (Ge) containing groups, Tin (Sn) containing groups, or Lead (Pb) containing groups, methods of preparing these precursor mixtures, and methods of preparing conductive conjugated copolymers using these precursor mixtures.

The precursors can be prepared from inexpensive starting materials, e.g. the corresponding difunctionalized silyl dihalide monomers. Furthermore, the precursors have many desirable mechanical properties, such as high thermal stability.

Also disclosed herein are conductive conjugated copolymers that are obtained via conversion of the precursor mixtures via chemical oxidation, electrochemical oxidation, or bromine conversion. For example, a conductive conjugated copolymers can be obtained via electrochemical oxidation of a precursor mixture in the solid-swollen state. In another embodiment, a conjugated copolymer can be obtained via exposure of the precursor mixture to bromine with heat treatment. Furthermore, the solid-state conversion of the precursor mixture to a conductive conjugated copolymer results in a greater yield of conductive polymer as compared to other known processes to prepare conductive polymer.

The precursor mixtures are easily processed into films using standard techniques such as cast, spin, dip, inkjet, spray, screen print, melt processing, and other well-known processes.

Disclosed herein is a precursor mixture comprises two precursors, wherein a first precursor is

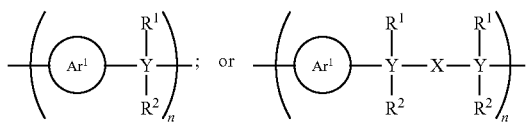

wherein $Ar^1$ is a heteroaryl electron donor unit (e.g. EDOT, BEDOT, or derivatives thereof); each occurrence of $R^1$ and $R^2$ is independently $C_1$-$C_{12}$ alkyl, $C_1$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater; and wherein a second precursor is

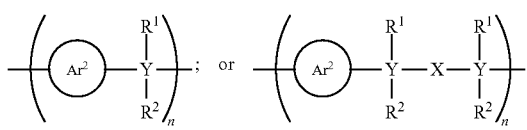

wherein $Ar^2$ is a heteroaryl electron acceptor unit (e.g. BTD, BEBTD, BPBTD, or derivatives thereof); each occurrence of $R^1$ and $R^2$ is independently $C_1$-$C_{12}$ alkyl, $C_1$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater. The number of repeat units (n) of the precursor can be greater than about 10, specifically greater than about 15. Specifically n can be about 10 to about 350, more specifically about 15 to about 300, and yet more specifically about 20 to about 250.

In one embodiment, $R^1$ and $R^2$ are independently $C_1$-$C_{12}$ alkyl; more specifically methyl, ethyl, propyl, butyl, hexyl, or octyl, and yet more specifically methyl or octyl; X is O; and Y is Si or Ge.

In another embodiment, the individual precursor can comprise Si and Ge in a ratio of about 1:99 to about 99:1 of Si:Ge, specifically a ratio of about 10:90 to about 90:10 of Si:Ge, more specifically a ratio of about 25:75 to about 75:25 of Si:Ge, and yet more specifically a ratio of about 40:60 to about 60:40 of Si:Ge.

A desired precursor size and weight can be obtained by varying the starting materials or preparation conditions. Furthermore, the precursors can have specific endgroups via use of an appropriate endcapping reagent. For example, a trimethylsilylchloride would provide a precursor that would have trimethylsilyl endgroups. Additionally, by adjusting the molecular weight of the precursor, the processing conditions can be changed. For example, for spray coating, low molecular weight, low viscosity precursors having a low n value can be prepared.

In one embodiment, the precursor mixture comprises 2 different precursors, one as a donor and another as an acceptor. In another embodiment, the precursor mixture comprises 3, 4, 5, or more precursors. Within this embodiment, at least one precursor is a donor and at least one precursor is an acceptor.

The precursor can be conveniently prepared from the corresponding heteroaryl monomers or derivatives thereof. In one embodiment, the heteroaryl monomer (H—Ar—H where Ar is $Ar^1$ or $Ar^2$ discussed herein) is deprotonated and reacted with an appropriate species $R^1R^2YZ_2$ in the presence of a base, which is then converted to the precursor.

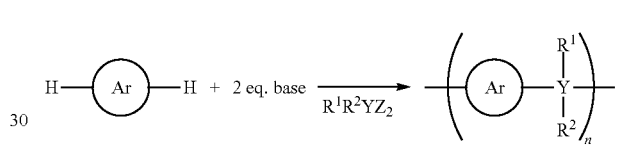

$R^1$ and $R^2$ are independently $C_1$-$C_{12}$ alkyl, $C_1$-$C_{12}$ haloalkyl, or aryl; Y is Si, Ge, Sn, or Pb; and each Z is independently Cl, Br, or I. Suitable bases include, for example, alkyl lithium (e.g. t-butyl Li, n-butyl Li, sec-butyl Li), lithium dialkyl amides (e.g. lithium diisopropylamide), or other base of equivalent basicity. Conditions for the preparation of the precursor are provided in more detail below.

The prepared precursor having the presence of the Si, Ge, Sn, or Pb units allows for high molecular weight polymers which can be processed as conventional polymers. Additionally, the precursors are soluble in a variety of solvents allowing for solution processing. Adjusting the lengths of the alkyl groups pendent from the Si, Ge, Sn, or Pb allows for the tailoring of solubility in organic solvents. Additionally, many of the precursors have a melt transition allowing for melt processing such as by compression molding, injection molding, melt spinning, and the like.

The units of Si, Ge, Sn, or Pb in the precursor allows for rotation in the precursor backbone while the heteroaryl is a rigid portion in the backbone. Such a combination of groups is similar to a flexible/rigid main chain liquid crystal. The heteroaryl groups in the precursor can crystallize to give a semicrystalline material. Such crystallinity translates to higher conductivities as compared to amorphous conjugated polymers. Therefore, the crystallinity can possibly be maintained when the precursor is converted to the conductive polymer which is more pi conjugated, thereby enhancing the conductivity of the formed conductive copolymer.

The heteroaryl (Ar, $Ar^1$ and $Ar^2$ groups) is selected according to the donor-acceptor approach, and can be chosen to result in a conductive copolymer having desired physical and electrochemical properties. Exemplary heteroaryl monomers used to prepare the precursors include those disclosed below, as well as derivatives thereof. Exemplary derivatives include replacement of an aryl hydrogen with a halogen for example which can be converted to the corresponding organometallic (e.g. addition of magnesium to form a di-Grignard reagent for ambient temperature processes).

Suitable heteroaryl monomers to prepare electron donor-precursors include EDOT, BEDOT, ProDOT-Me$_2$, etc. or substituted derivatives thereof, as well as thiophene, furan, pyrrole, indole, etc. or substituted derivatives thereof 3,4-Ethylenedioxythiophene, 3,4-ethylenedithiathiophene, 3,4-ethylenedioxypyrrole, 3,4-ethylenedithiapyrrole, 3,4-ethylenedioxyfuran, 3,4-ethylenedithiafuran, and derivatives having the general structure:

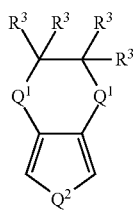

wherein each occurrence of $Q^1$ is independently S or O; $Q^2$ is S, O, or N—$R^4$ wherein $R^4$ is hydrogen or $C_1$-$C_6$ alkyl; and each occurrence of $R^3$ is hydrogen, $C_1$-$C_{12}$ alkyl, $C_1$-$C_{12}$ haloalkyl, $C_1$-$C_{12}$ alkoxy, $C_1$-$C_{12}$ haloalkoxy, aryl, —$C_1$-$C_6$ alkyl-O—$C_1$-$C_6$ alkyl, or —$C_1$-$C_6$ alkyl-O-aryl.

Suitable heteroaryl monomers to prepare electron acceptor-precursors include BTD, BEBTD, BPBTD, etc. or substituted derivatives thereof, as well as imidazole, triazine, tetrazine, quinoline, thiazole, oxazole, pyridine, thiadiazole, etc. or substituted derivatives thereof.

In one embodiment, donor-precursors have the general structures below:

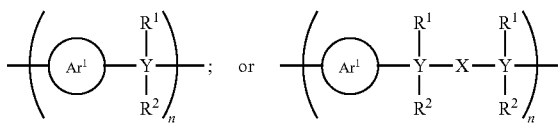

wherein $Ar^1$ is a donor unit (e.g. EDOT, BEDOT, thiophene, furan, pyrrole, indole, etc. or derivatives thereof); each occurrence of $R^1$ and $R^2$ is independently $C_1$-$C_{12}$ alkyl, $C_1$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater.

Exemplary donor-precursors include those having the following general structures:

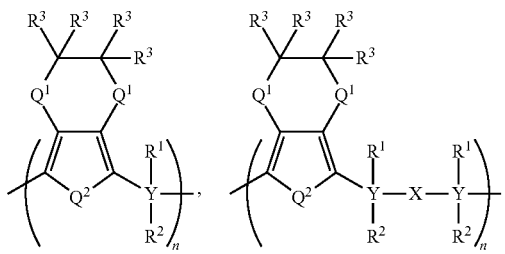

wherein $Q^1$, $Q^2$, $R^1$, $R^2$, $R^3$, X, n, and Y are as defined above.

In one embodiment, acceptor-precursors have the general structures below:

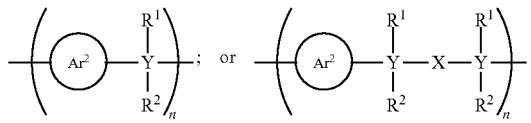

wherein $Ar^2$ is an acceptor unit (e.g. BTD, BEBTD, BPBTD, imidazole, triazine, tetrazine, quinoline, thiazole, oxazole, pyridine, thiadiazole, etc. or derivatives thereof) each occurrence of $R^1$ and $R^2$ is independently $C_1$-$C_{12}$ alkyl, $C_1$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater.

In another embodiment, acceptor-precursors have the general structures below:

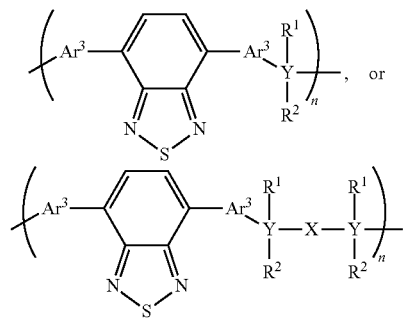

wherein $Ar^3$ is any electron rich heterocycle (e.g. thiophene, etc.) or derivatives thereof; each occurrence of $R^1$ and $R^2$ is independently $C_1$-$C_{12}$ alkyl, $C_1$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater.

An exemplary random copolymer having the following general structure can be prepared:

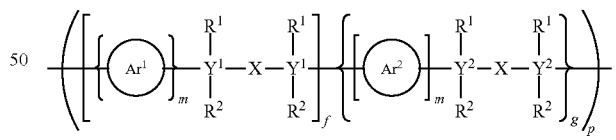

wherein $Ar^1$ and $Ar^2$ each independently is a heteroaryl group as previously described; each occurrence of $R^1$ and $R^2$ is independently $C_1$-$C_{12}$ alkyl, $C_1$-$C_{12}$ haloalkyl, or aryl; each occurrence of $Y^1$ and $Y^2$ is independently Si, Ge, Sn, or Pb; the ratio of f:g is about 5:95 to about 95:5; and p is about 5 or greater. As these are random copolymers, f and g represent the total number of units, not necessarily connected to each other, within the polymer. In one embodiment, $Ar^1$ is EDOT or BEDOT; $Ar^1$ is BTD, BEBTD, or BPBTD; both $R^1$ and $R^2$ are methyl groups; $Y^1$ is Si and $Y^2$ is Si.

As used herein, "alkyl" includes straight chain, branched, and cyclic saturated aliphatic hydrocarbon groups, having the specified number of carbon atoms, generally from 1 to about 12 carbon atoms for the straight chain and generally from 3 to about 12 carbon atoms for the branched and cyclic. Examples of alkyl include, but are not limited to, methyl, ethyl, n-propyl, isopropyl, n-butyl, 3-methylbutyl, t-butyl, n-pentyl, sec-pentyl, cyclopentyl, cyclohexyl, and octyl. Specific alkyl groups include lower alkyl groups, those alkyl groups having from 1 to about 8 carbon atoms, from 1 to about 6 carbon atoms, or from 1 to about 4 carbons atoms.

As used herein "haloalkyl" indicates straight chain, branched, and cyclic alkyl groups having the specified number of carbon atoms, substituted with 1 or more halogen atoms, generally up to the maximum allowable number of halogen atoms ("perhalogenated", e.g. perfluorinated). Examples of haloalkyl include, but are not limited to, trifluoromethyl, difluoromethyl, 2-fluoroethyl, and pentafluoroethyl.

As used herein, "alkoxy" includes an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Haloalkoxy" indicates a haloalkyl group as defined above attached through an oxygen bridge.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, fluorene, and bi-phenyl.

As used herein, "heteroaryl" indicates a stable 5- to 7-membered monocyclic aromatic ring which contains 1, 2, or 3 heteroatoms chosen from N, O, and S, with remaining aromatic ring atoms being carbon, or a stable bicyclic or tricyclic system containing at least one 5 to 7 membered aromatic ring which contains 1, 2, or 3 heteroatoms chosen from N, O, and S, with remaining aromatic ring atoms being carbon. When the total number of S and O atoms in the heteroaryl group exceeds 1, these heteroatoms are not adjacent to one another.

"Halo" or "halogen" as used herein refers to fluoro, chloro, bromo, or iodo.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

Disclosed herein are precursor blends comprising two or more precursors. Additionally, blends comprising at least one of the foregoing precursors and an additional polymer are also contemplated. The additional polymer may be a conductive polymer, a nonconductive polymer, a thermoplastic or combinations comprising at least one of the foregoing.

The precursor can be conveniently prepared from the corresponding heteroaryl monomers or derivatives thereof.

In one embodiment, the heteroaryl monomer is doubly deprotonated and reacted with an appropriate species $R^1R^2YZ_2$ in the presence of a base, which is then converted to the precursor. $R^1$ and $R^2$ are independently $C_1$-$C_{12}$ alkyl, Y is Si, Ge, Sn, or Pb; and each Z is independently Cl, Br, or I. Suitable bases include, for example alkyl lithium (e.g. t-butyl Li, n-butyl Li, sec-butyl Li), lithium dialkyl amides (e.g. lithium diisopropylamide), or other base of equivalent basicity). The precursor obtained above can be purified by precipitation from solvent using a nonsolvent, for example, pentane/hexanes, followed by washing with nonsolvent via continuous procedure, for example, such as Soxhlet extraction.

The precursor mixtures can be converted to conductive conjugated copolymers by an oxidative [Ox] reaction process effected by chemical or electrochemical oxidation or by bromine conversion. For simplicity, the following illustration of an oxidative reaction process is described for a simple one-precursor system rather than a precursor mixture.

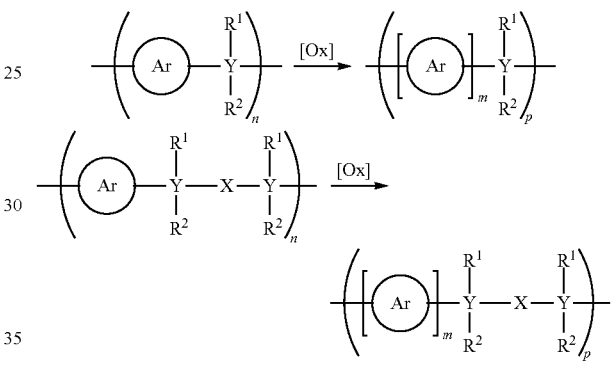

wherein Ar, $R^1$, $R^2$, X, Y, n, m, and p are as defined previously. The oxidative reaction process of precursor mixtures results in the formation of conjugated copolymers having a random distribution of donor and acceptor.

Conversion of the precursor mixtures to a conjugated copolymer results in the conjugated copolymer retaining some fraction of the Si, Ge, Sn, or Pb units in the backbone structure of the conjugated copolymer. The resulting conjugated copolymer has sigma conjugation rendering it different from other conjugated copolymers prepared from heteroaryl compounds via other processes.

Retention of some of the Si, Ge, Sn, or Pb units in the conductive copolymer resulting from the conversion of the precursor mixtures has some benefits. First, the conductive copolymer retains much of its high molecular weight as the number of repeat units is approximately the same between the precursor and the conductive copolymer. The high molecular weight provides the conductive copolymer with better mechanical properties. Second, the Si, Ge, Sn, or Pb is conjugated with the pi system of the heteroaryls and the atoms are in a tetrahedral geometry. This serves to have longer conjugation lengths than fully pi conjugated polymers resulting in the conductive copolymer prepared from the precursors to have lower oxidation potentials and therefore higher lying highest occupied molecular orbitals (HOMO).

In one method, the precursor mixture is chemically oxidized in a liquid. Suitable oxidants include the iron (III) salts of organic acids, inorganic acids containing organic residues, and inorganic acids, such as $FeCl_3$, $Fe(ClO_4)_3$. Oxidants such as $H_2O_2$, $K_2Cr_2O_7$, alkali or ammonium persulfates, alkali perborates, potassium permanganate, $NOBF_4$, or copper salts such as copper tetrafluoroborate may also be used. In addition, bromine, iodine, and oxygen may advantageously be used as oxidants. Persulfates and the iron (III) salts of organic acids and inorganic acids containing organic residues are preferred because they are not corrosive. Examples of suitable iron (III) salts of organic acids are the Fe(III) salts of $C_1$-$C_{30}$ alkyl sulfonic acids, such as methane or dodecane sulfonic acid; aliphatic $C_1$-$C_{20}$ carboxylic acids, such as 2-ethylhexylcarboxylic acid; aliphatic $C_1$-$C_{20}$ perfluorocarboxylic acids, such as trifluoroacetic acid and perfluorooctanoic acid; aliphatic dicarboxylic acids, such as oxalic acid; and aromatic, optionally $C_1$-$C_{20}$ alkyl-substituted sulfonic acids, such as benzenesulfonic acid, p-toluene-sulfonic acid and dodecyl benzenesulfonic acid. Mixtures of the aforementioned Fe(III) salts of organic acids may also be used. Examples of iron (III) salts of inorganic acids containing organic residues are the iron (III) salts of sulfuric acid semiesters of $C_1$-$C_{20}$ alkanols, for example the Fe(III) salt of lauryl sulfate.

Suitable liquids for conducting the oxidative chemical reaction do not adversely affect the reaction, and are specifically inert. Suitable liquids are further selected on the basis of economics, environmental factors, and the like, and may be organic, aqueous, or a mixture thereof. Suitable organic liquids may be aliphatic alcohols such as methanol and ethanol; aliphatic ketones such as acetone and methyl ethyl ketone; aliphatic carboxylic esters such as ethyl acetate; aromatic hydrocarbons such as toluene and xylene; aliphatic hydrocarbons such as hexane; aliphatic nitriles such as acetonitrile; chlorinated hydrocarbons such as dichloromethane; aliphatic sulfoxides such as dimethyl sulfoxide; and the like, as well as mixtures comprising at least one of the foregoing organic liquids. Specifically aqueous liquids are used, that is, a liquid comprising water and/or water-miscible organic liquids such as lower alcohols, acetonitrile, tetrahydrofuran, dimethylacetamide, dimethyl formamide, and the like.

Heat may not be necessary for all conductive copolymers in chemical oxidation processes. However, it can be used to speed up the conversion to conductive copolymers. Heat can be administered to the polymer either during its exposure to chemical oxidants or after the exposure. Typical reaction conditions include temperatures of 0 to about 100° C. The oxidation is continued for a period of time until the desired conductive copolymer is prepared. The degree of conversion varies depending upon the end use application, and is readily determined by one of ordinary skill in the art without undue experimentation. The polymerization time may be a few minutes up to about 48 hours, and depends on a number of factors including the size of the reactor utilized, the reaction temperature, the oxidant utilized, and the like.

In one embodiment, the precursor mixtures are converted to conductive conjugated copolymers by exposure to bromine. The bromine can be administered by either gas phase exposure of the mixture to bromine or by placing bromine in solution and exposing the precursor mixture to the solution. The precursor mixture may dissolve in the solution or does not dissolve but only swells.

In another embodiment where bromine and heat are used to oxidize the precursor mixtures into conductive copolymers, the precursor mixture comprises Si-containing precursors.

In yet another embodiment where bromine and heat are used to oxidize the precursor mixtures into conductive copolymers, the precursor mixture comprises Ge-containing precursors.

In one embodiment, the precursor mixtures are converted to conductive conjugated copolymers by a chemical oxidant such as $FeCl_3$ or those previously discussed. When a chemical oxidant is used, the addition of a salt to the reaction solution is used to get adequate oxidation of the precursors. Suitable salts for this purpose include organic soluble salts, inorganic salts, ionic liquids, and polyelectrolytes such as polystyrene sulfonate, polyacrylic acid sodium salt, poly (meth)acrylic acid sodium salt, etc. Exemplary salts include tetra-alkyl ammonium, ammonium, lithium, or sodium cations with tetrafluoroborate, hexafluorophosphate, perchlorate, halides, toluenesulfonate and other aliphatic sulfonate salts, trifluoromethylsulfonate, bistrifluoromethanesulfonimide, sulfates, carbonates or persulfates.

In another embodiment, the precursor mixtures are converted to conductive copolymers by chemical oxidant $NOBF_4$.

The precursor mixtures, specifically the Si-containing precursors, can be converted to conjugated and conductive copolymers in the solid state by employing a water/oxidant solution. When the precursor mixture is cast, a salt such as those previously described, is added during the casting process. The cast precursor mixture can then be oxidized with a suitable oxidant to result in the conductive copolymer. This process results in a clean, efficient method to convert to the precursor into a conductive copolymer film.

An alternative method for preparing the conductive conjugated copolymer is by electrochemical oxidation to convert the precursors of the mixture to the conductive conjugated copolymer. Conventional electrolytic cells can be used for the reaction. In one embodiment, a three-electrode configuration (working electrode, counter electrode, and reference electrode) in operable communication with an electrolyte is used, comprising a working electrode, specifically a button working electrode selected from the group consisting of platinum, gold, vitreous carbon, and indium doped tin oxide working electrodes or non-button electrodes such as the ITO, and platinum flag, a platinum flag counter electrode, and an Ag/Ag+ non-aqueous reference electrode.

Suitable electrolytes include tetraalkylammonium salts, e.g., tetraethylammonium, tetrapropyl ammonium, tetrabutylammonium salts, as well as salts of cations such as lithium trifluoromethansulfonate. Suitable counter ions include but are not limited inorganic ions such as bistrifluoromethylsulfonimide, tosylate, perchlorate, tetrafluoroborate, hexafluorophosphate, and halides such as chloride, bromide, iodide, and organic anions such as tosylate, triflate, trifluoromethylsulfonimide, or polyanions, e.g., polystyrenesulfonate, the anionic form of acrylic acid. Solvents may be used to prepare an electrolyte solution, for example water, ethanol, methanol, acetonitrile, propylene carbonate, tetraglyme, methylene chloride, chloroform, and tetrahydrofuran. Specified solvents are water, acetonitrile, and propylene carbonate.

Other suitable electrolytes include ionic liquids such as butylmethylimidazolium hexafluorophosphate (BMIM $PF_6$) and butylmethylimidizolium tetrafluoroborate (BMIM $BF_4$).

Specific electrolytes include tetrabutylammonium perchlorate/acetonitrile, tetrabutylammonium tetrafluoroborate, tetrabutylammonium hexafluorophosphate/acetonitrile, lithium trifluoromethansulfonate/acetonitrile, and lithium triflate/acetonitrile. Exemplary concentrations of the electrolytes are 0.1 M.

A specific working electrode is a vitreous carbon electrode and the electrolyte is tetrabutylammonium perchlorate/acetonitrile. Another specific working electrode is a platinum button electrode and the electrolyte is lithium trifluoromethansulfonate/acetonitrile.

In one embodiment, the prepared precursor mixture can be coated onto a substrate prior to the oxidation step. The precursor mixture can be applied via ink jet printing, screen printing, roll to roll printing processes, spin coating, meniscus and dip coating, spray coating, brush coating, doctor blade application, curtain casting, spray casting, and the like, to form a layer. The precursor mixture film on the substrate can then be converted to a conductive conjugated copolymer in solid state via any one of the processes previously described.

The precursor mixtures, specifically the Si-containing precursors, can be converted to conjugated and conductive copolymers in the solid state by placing them in a water/salt solution and applying a potential at or above the oxidation of the aryl constituent of the precursor. When the precursor mixture is cast, a salt can be added during the casting process. Exemplary salts include tetra-alkyl ammonium, ammonium, lithium, or sodium cations with tetrafluoroborate, hexafluorophosphate, perchlorate, halides, toluenesulfonate and other aliphatic sulfonate salts, trifluoromethylsulfonate, bistrifluoromethanesulfonimide, sulfates, carbonates or persulfates.

Optionally, the precursor mixture can be converted to the conducting conjugated copolymer which in turn can be further used for preparing films or coating various substrates.

The precursor mixtures are melt processable, such as by compression molding, injection molding, melt spinning, and melt drawing of fibers, and the like. Another method of preparing fibers includes electrospinning the precursor mixtures which can then be converted to conducting conjugated copolymers.

In another embodiment, the precursor mixtures can be formed into liquid crystals upon heating.

The precursor mixtures can be either amorphous or semicrystalline depending upon its chemical structure.

Amorphous precursor mixtures can be prepared by substituting the heteroaryl with branched alkyl groups. The branching will reduce the precursor viscosity and can disrupt crystallinity. Such amorphous precursor mixtures can potentially be processed using supercritical fluid as a solvent (e.g. supercritical $CO_2$). Additionally, the siloxane-containing (Si—O—Si) precursors are also candidates for processing using supercritical fluids.

The described process of preparing conjugated copolymers from the precursor mixtures is amenable to a wide variety of aromatic moieties indicating the possibility of making a large number of different conjugated copolymers using this technique. Furthermore, solubility and physical properties such as the glass transition temperature of the precursor can be modified by using Si, Ge, Sn, and Pb group with different substituents attached.

Suitable substrates that can be coated include solid materials (flexible or rigid), and may be, for example, glass, an organic polymer such as a plastic, silicon, a mineral, a semiconducting material, a ceramic, a metal, a metal oxide, and the like, as well as a combination of two or more of the foregoing materials. The substrate may be inherently conductive or may be insulating.

As many of the precursors are soluble yet the conjugated copolymers prepared from the precursor are insoluble, preparation of conjugated copolymer via electropolymerization in the solid-swollen state can be used to pattern one conjugated copolymer on top of another without affecting the previous layer. Such a process is a prerequisite in making multilayer electronic devices.

Films and materials comprising the above-described conductive copolymers can be utilized in a variety of applications, including antistatic coatings, electrically conductive coatings, electrochromic devices, photovoltaic devices, light emitting diodes for display applications, hole injection layers for light emitting diodes, near infrared light emitting diodes, transparent conductive coating for indium doped tin oxide replacement, flat panel displays, flexible displays, photoimageable circuits, printable circuits, thin film transistor devices, batteries, electrical switches, capacitor coatings, corrosion resistant coatings, electromagnetic shielding, sensors, biosensors, dimmable mirrors, type III supercapacitors, LED lighting, windows, printing, eyewear, camera filters, and the like. The electrical conductivity of the copolymers can be readily modified, if necessary, to meet the requirements of any of the previously mentioned application by doping the polymers with conventional dopants such as anions (for p-doped polymers) and cation dopants (for n-doped polymers) known in the art.

The following illustrative examples are provided to further describe the invention and are not intended to limit the scope of the claimed invention.

EXAMPLES

Example 1. Preparation of a Siloxane Precursor Prepared from bis-3,4-ethylenedioxythiophene ("BEDOT") and a Siloxane Precursor Prepared from bis-(3,4-ethylenedioxythiophene)-2,1,3-benzothiadiazole ("BEBTD")

BEDOT (xmol) was taken in a vacuum dry three-neck 250 ml round bottom flask followed by cannulating anhydrous tetrahydrofuran (THF). n-Butyl lithium (n-BuLi) (2×mol) was added dropwise into the reaction mixture at −78° C. (dry ice-acetone bath). The reaction mixture was stirred for one hour at room temperature followed by dropwise addition of dimethyldichlorosilane (1×mol) over a period of 15 minutes. The reaction was quenched after stirring at room temperature for 48 hours under nitrogen atmosphere using water. The EDOT precursor was obtained by precipitating out from solution using n-pentane. The precursor prepared from BEDOT ("PRE-BEDOT") was dried under vacuum, and purified by washing with pentane or pentane—THF (50-50) mixture.

Siloxane precursor prepared from BEBTD ("PRE-BEBTD") was synthesized according to a similar procedure used for BEDOT above. EDOT (1, y mol) was reacted with n-butyl lithium (2y mol) followed by 1,3-dichlorotetramethyldisiloxane (0.5 y mol) to form 1,3-diEDOT tetramethyldisiloxane (2, y' mol) which is then reacted with n-butyl lithium (2y' mol) followed by trimethyltin chloride (2.1 y' mol) to yield intermediate 3. Intermediate 3 (y" mol) is then reacted with 4,7-dibromo-2,1,3-benzothiadiazole in the presence of tetrakis(triphenylphosphine)palladium to form PRE-BEBTD.

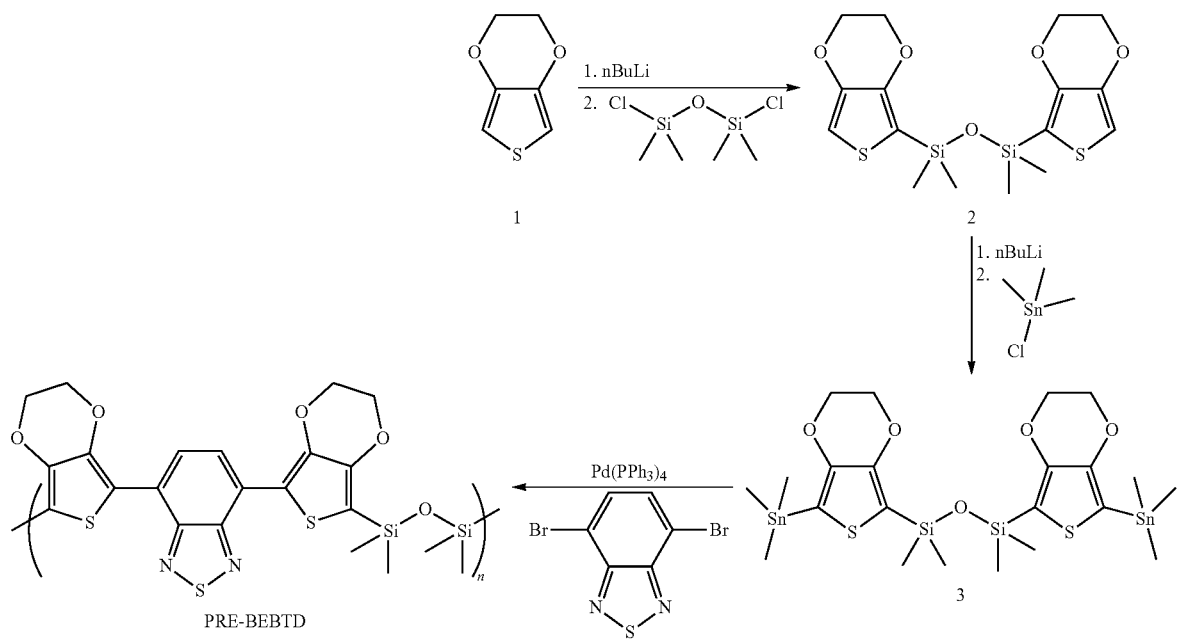

Example 2. Determination of Donor and Acceptor Siloxane Precursors

Two donors EDOT and ProDOT-Me$_2$ were used to investigate the absorbance change under influence of acceptor BTD in conjugated system. The structures of PEDOT, poly(BEBTD), poly(ProDOT-Me2), and poly(BPBTD) are provided below.

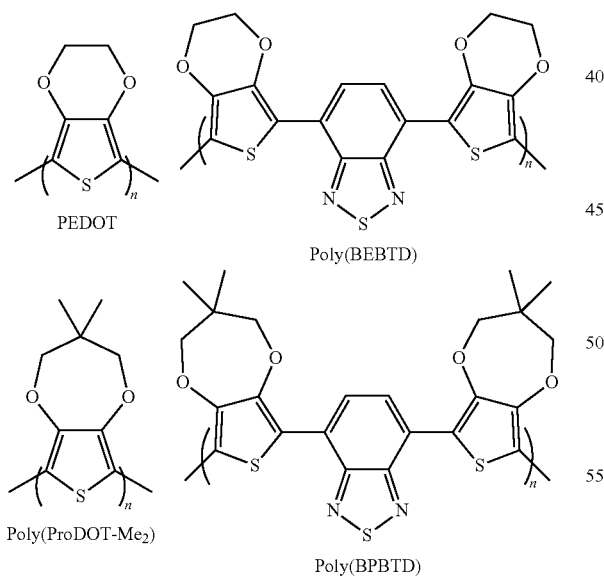

Figure 1B:
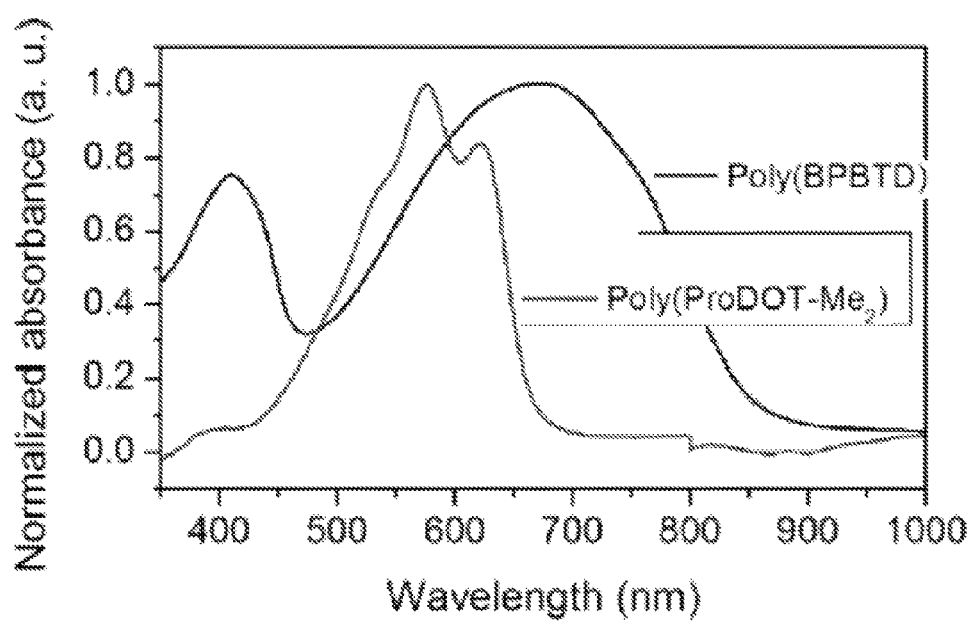
FIG. 1b illustrates the UV-vis-NIR spectra of poly(ProDOT-Me$_2$) and poly(BPBTD).

The polymers containing EDOT as donor exhibit three λmax of 595 nm from PEDOT, and 430 and 775 nm from poly(BEBTD) (see the UV-vis-NIR spectra of PEDOT and poly(BEBTD) in FIG. 1a). Spectrum of PEDOT locates at the lack of absorption coverage of poly(BEBTD). This suggests that EDOT as donor and BTD as acceptor system may be promising materials to achieve black electrochromic. ProDOTMe$_2$ and BTD system also offers three λmax of 573 nm from poly(ProDOT-Me2), and 410 and 673 nm from poly(BPBTD), while it shows ineffective coverage in visible region especially at ca. 480 nm (see the UV-vis-NIR spectra of Poly(ProDOT-Me$_2$) and poly(BPBTD) in FIG. 1b). The EDOT-BTD system was chosen due to the uniform absorption in the entire visible region which allows for the achievement of black.

Siloxane precursors PRE-BEDOT and PRE-BEBTD were chosen as the donor-acceptor duo. PRE-BEDOT was chosen over EDOT-PP as it has a higher Tg, allowing it to maintain its solid form at room temperature. PRE-BEDOT exhibits a low conversion potential close enough to that of PRE-BEBTD such that it can avoid unnecessary over-oxidation at high potential.

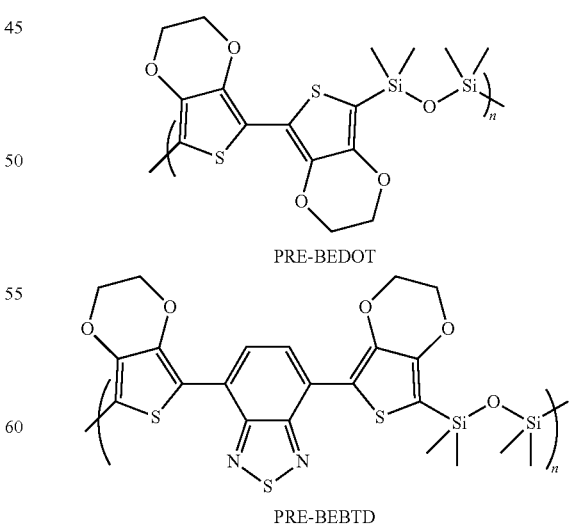

Figure 2:
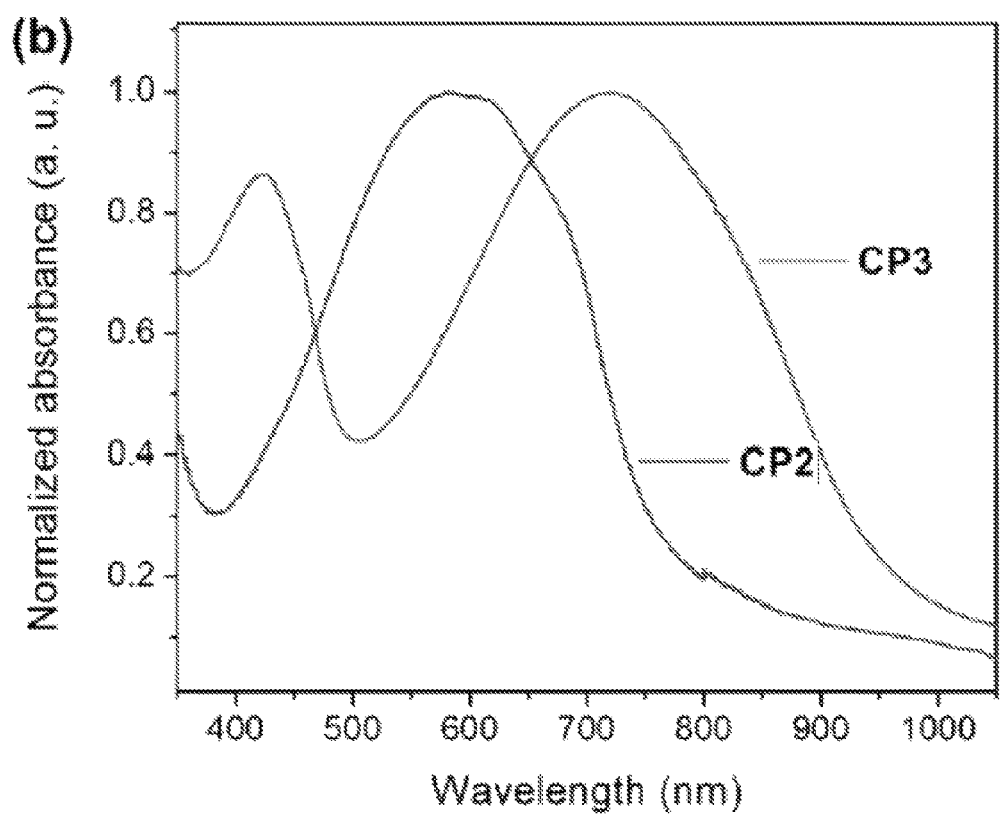
FIG. 2 illustrates the absorption spectra of resulting conjugated polymers CP2 and CP3 by electrochemical conversion of PRE-BEDOT and BEBTD-P, respectively.

The absorption spectra of the resulting conjugated polymers by electrochemical conversion of PRE-BEDOT (CP2)

and PRE-BEBTD (CP3) are shown in FIG. 2. The absorption spectra are similar to those of PEDOT and poly(BEBTD), respectively, and covers the entire visible spectrum rather evenly.

The composition of the donor and acceptor will be determined by the mixed ratio of PRE-BEDOT and PRE-BEBTD. Since the two precursors are soluble in low boiling chloroform suitable for spray coating, PRE-BEDOT and PRE-BEBTD solutions of same molarity in terms of molecular weight of repeating units were prepared and mixed to optimize the composition of donor and acceptor. The ratios of PRE-BEDOT to PRE-BEBTD, and EDOT to BTD in each blend solution are summarized in Table 1 below. Five mM of solutions of the precursors in chloroform were used. The molarity (M) is in terms of molecular weight of repeating unit of each siloxane precursor.

TABLE 1

| Blend | Volume ratio of PRE-BEDOT | Volume ratio of PRE-BEBTD | EDOT:BTD |
|---|---|---|---|
| BLD110 | 1 | 1 | 4:1 |
| BLD115 | 1.5 | 1 | 5:1 |
| BLD120 | 2 | 1 | 6:1 |
| BLD125 | 2.5 | 1 | 7:1 |
| BLD130 | 3 | 1 | 8:1 |
| BLD140 | 4 | 1 | 10:1 |

Figure 3:
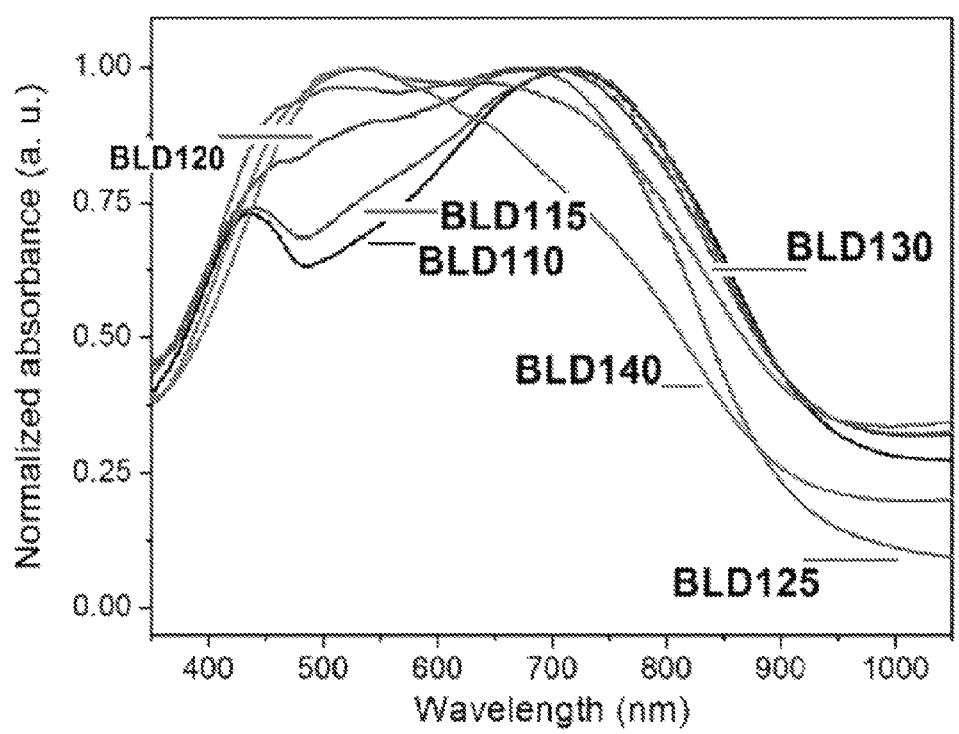
FIG. 3 illustrates the UV-vis-NIR spectra of the conjugated copolymers by electrochemical conversion of the mixed solution of PRE-BEDOT and PRE-BEBTD.

Each blend solution was spray coated onto ITO-coated glass and converted by applying potential of 0.5 V for 10 sec via chronocoulometic method. The absorption spectra of the resulting conjugated copolymers at neutral state exhibited broad absorption over visible region (see the UV-vis-NIR spectra in FIG. 3). Spectra of conjugated copolymers from BLD110 and BLD115 exhibit two distinct absorption bands at ca. 435 and 721 nm and diminishing of deficient absorption around the wavelength of ca. 500 nm as the ratio of EDOT to BTD increases. As a result of further addition of EDOT to BTD, broad even absorption along with the trace of two peak at 435 and 721 nm were observed for conjugated copolymers from BLD120, BLD125, and BLD130. Spectrum of the conjugated copolymer from BLD140 exhibits new $\lambda$max of 530 nm and broad absorption up to the wavelength of ca. 930 nm. Even the conjugated copolymer from BLD140 contains one acceptor per ten donor unit, BTD acceptor sufficiently affect electronic structure and extend Π-conjugation of the system.

Figure 4:
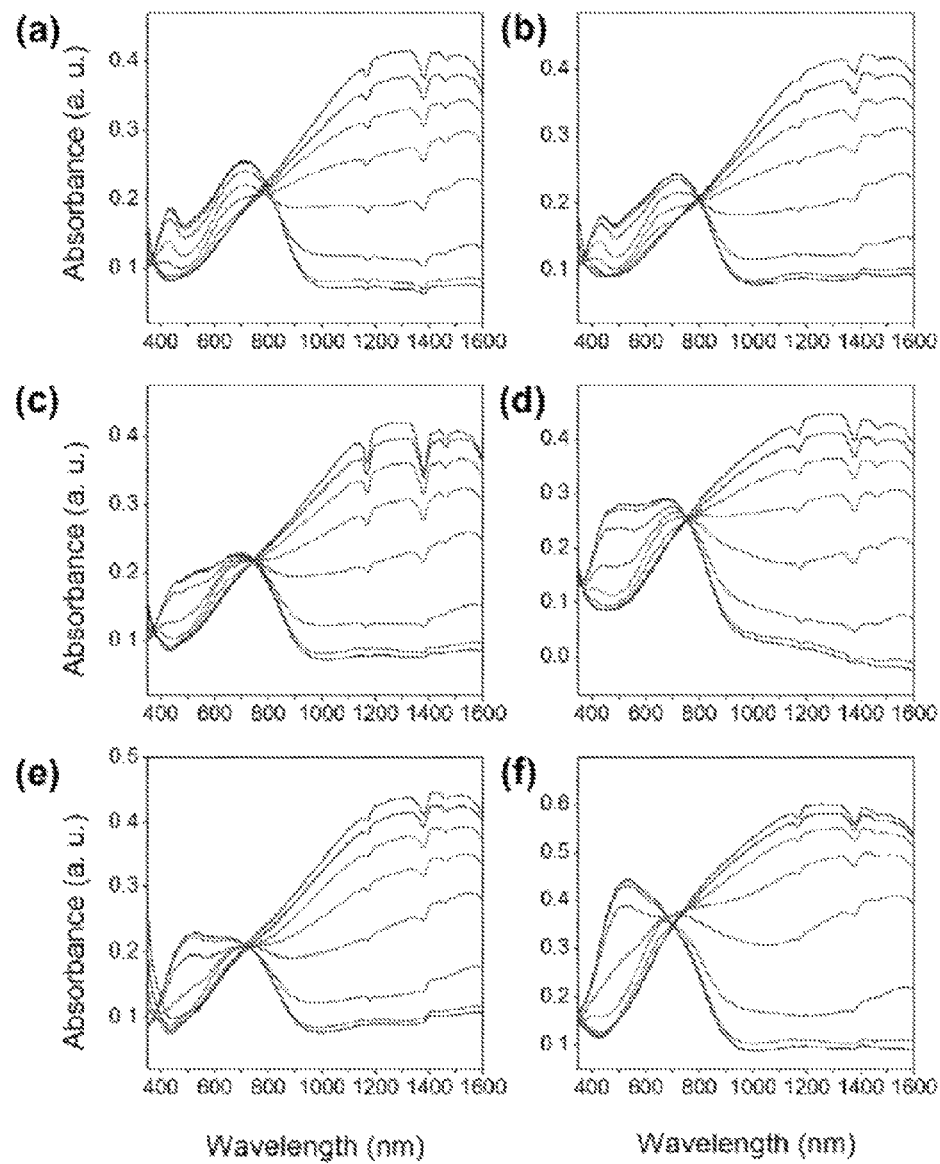
FIG. 4 illustrates the spectroelectrochemistry of the conjugated copolymers converted from the various blends of PRE-BEDOT and PRE-BEBTD: (a) BLD110, (b) BLD115, (c) BLD120, (d) BLD125, (e) BLD130, and (f) BLD140.

The band gap of resulting conjugated copolymers are in a range of 1.30-1.32 eV. It was noted that bathochromic shift of short wavelength peak and hypsochromic shift of long wavelength peak of the dual band absorption are generally shown if donor was added to acceptor regularly in the conjugated system. Conjugated copolymers of blends show negligible shift of the short and long wavelength peak by changing the ratio of EDOT to BTD. This suggests that the distribution of donor and acceptor in the conjugated copolymer from the blend is random, therefore the conjugated copolymer from a blend offers broad coverage in the visible region. Among various blend solutions, BLD120, BLD125, and BLD130 results in conjugated copolymers that absorb evenly in the visible region. All resulting conjugated copolymers show absorption spectra changes by redox process upon changing applied potential and depicted in FIG. 4.

Figure 5:
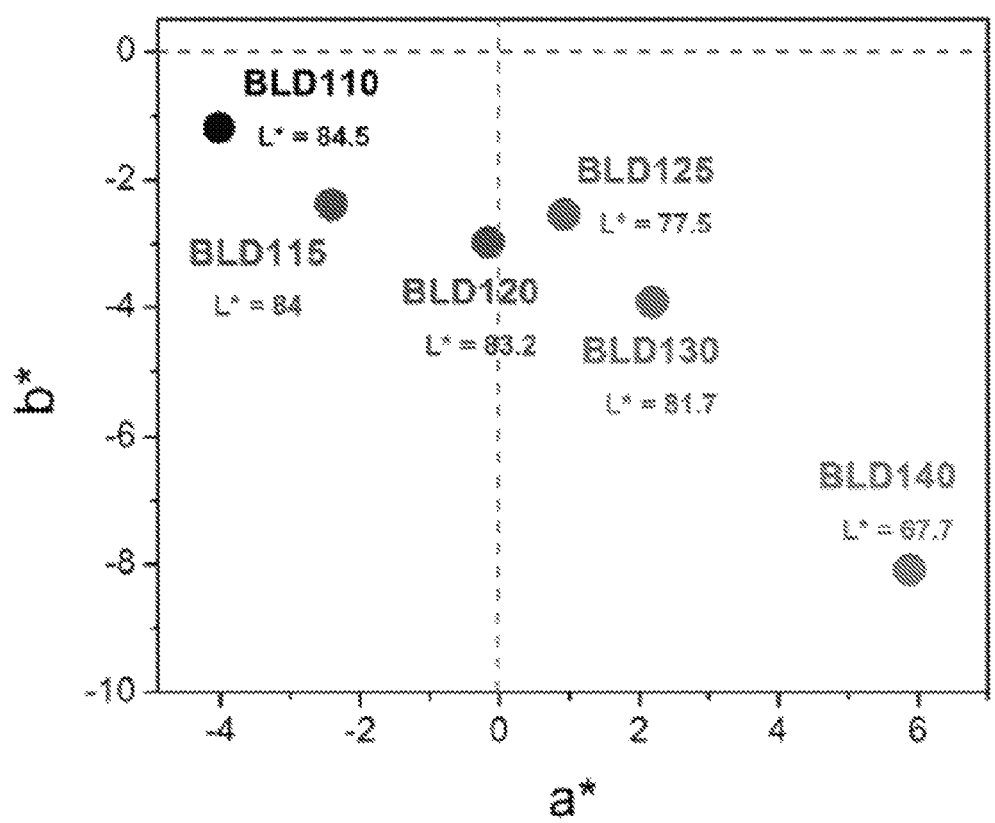
FIG. 5 illustrates the CIE1976 color coordinates (L*a*b*) of the conjugated copolymers from various blends of PRE-BEDOT and PRE-BEBTD.

To establish the correlation of the composition of donor and acceptor and the resulting color, color coordinate of the conjugated copolymers from the blends of Table 1 were characterized and CIE L*a*b* color space are depicted in FIG. 5. As a* and b* in CIE L*a*b* reaches (0, 0) (white point), the saturation of color is even, therefore the color is close to black. Among conjugated copolymers from blends, BLD125 offers the conjugated copolymer having the most close value to white point, even considering the difference of L*. Although color space are not reaching to (0, 0), residual violet indicated by a* and b* of the conjugated copolymer from BLD125 (0.92, −2.53) is the least sensitive to human perception. Therefore, BLD125 was chosen for the material to following study.

Example 3. Sequential Conversion as Control Study

Figure 6:
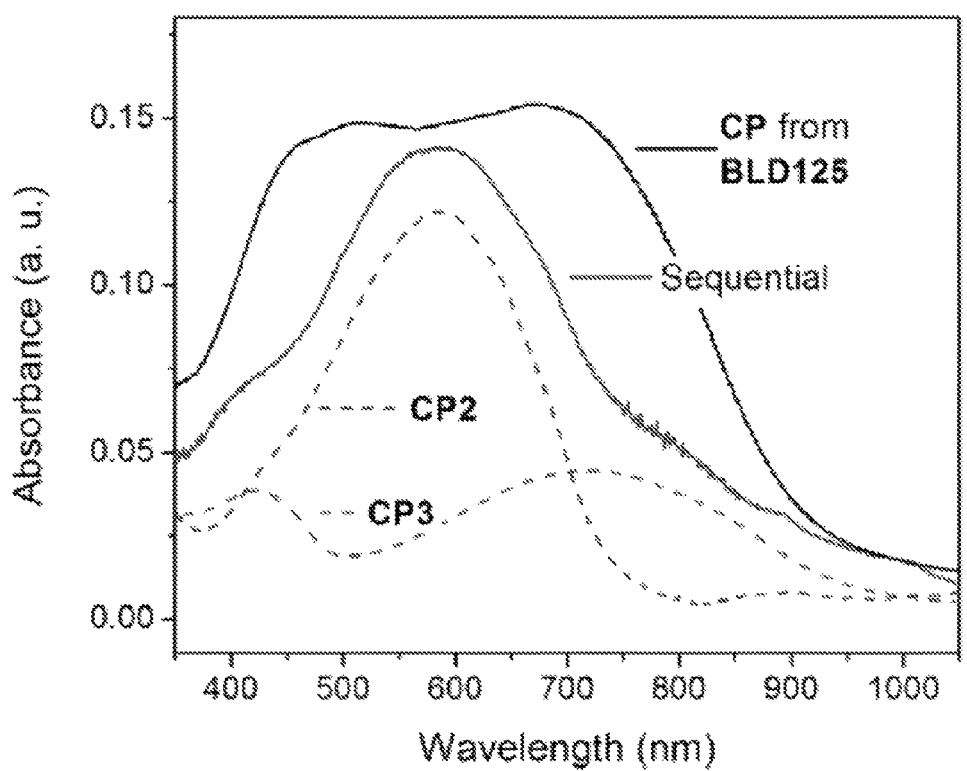
FIG. 6. illustrates absorption spectra of the conjugated copolymer from BLD125 (top solid line), sequentially converted CP2 and CP3 (lower solid line), CP2 (higher dashed line), and CP3 (lower dashed line).

To rule out the possibility of complimentary overlap of the two absorption spectra of CP2 and CP3 by the result of serendipity, a sequential conversion experiment was performed as a control. Since the best spectral overlap was shown in BLD125 with a 2.5:1 ratio of PRE-BEDOT and PRE-BEBTD, the same ratio was used for the control sample. A 1 mL of 5 repeating unit mM PRE-BEBTD solution was spin coated on ITO-coated glass and the film was subsequently converted to a conjugated polymer to form a CP3 film. After rinsing with clean ACN, 2.5 mL of 5 repeating unit mM PRE-BEDOT solution was spray coated on a top of CP3 film. The film was converted to a conjugated polymer and used for the control sample of sequential conversion. As shown in FIG. 6, sequential conversion exhibits the absorption spectrum distinctive from that of conjugated copolymer from BLD125. The control sample exhibits $\lambda$max of 587 nm along with shoulder peak of ca. 420 nm and ca. 775 nm. The result suggests that the absorption spectrum of the control sample of sequential conversion is the simple addition of absorption value at each wavelength of two conjugated polymers (CP2 and CP3). This proposes that the broad and even absorption of conjugated copolymers from the blends of the precursors is due to the random distribution of donor and acceptor with the proper ratio in the conjugated system. Further it suggests that a coupling of electroactive group in the siloxane precursors has taken place not only in intramolecular chain, but also in intermolecular chain, since the acceptor exists only in one siloxane precursor.

Figure 7:
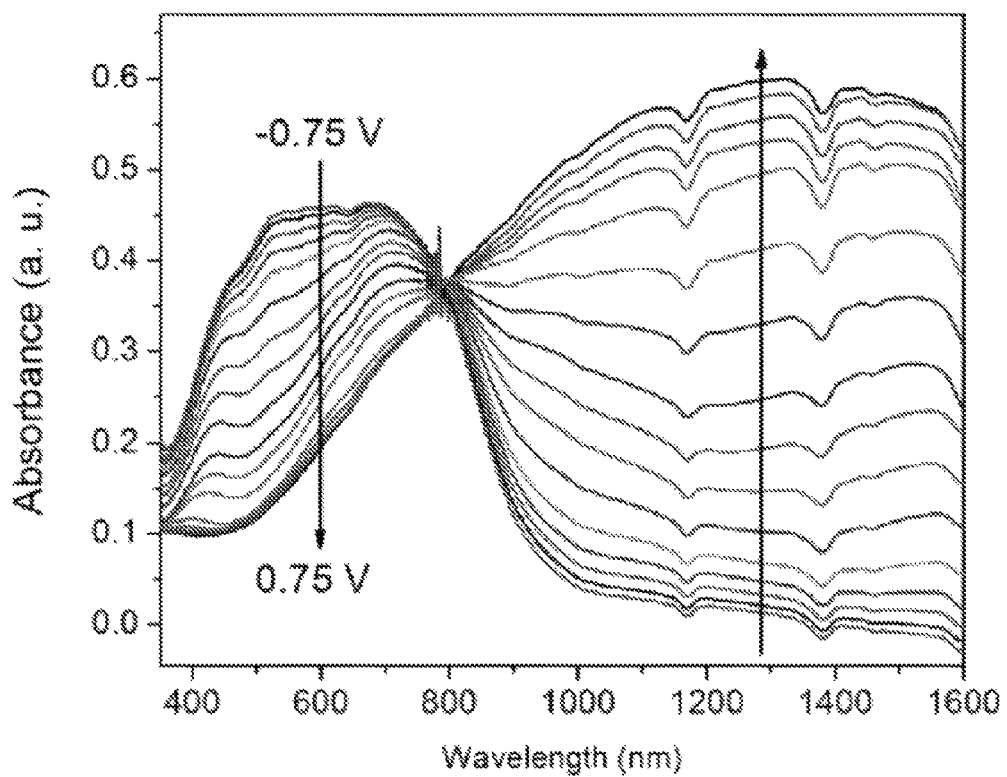
FIG. 7. illustrates the spectroelectrochemistry of the conjugated copolymer converted from BLD125.

Spectroelectrochemical and colorimetric analysis: The film of the conjugated copolymer electrochemically converted from BLD125 on ITO-coated glass by applying potential of 0.5 V for 10 seconds, was used for detained spectroelectrochemistry. The absorbance change of conjugated polymers was measured with the applied potential controlled by chronocoulometic technique. At its neutral state (−0.75 V), electrochemically prepared film from BLD125 exhibited strong absorption in the entire visible region evenly, which corresponds to $\pi$-$\pi$* transition. At this state, the copolymer exhibited a black color with an optical band gap at 1.30 eV as shown in FIG. 7. As sequential oxidation progresses upon potentiostatic increments, the suppression of the $\pi$-$\pi$* transition was observed. In addition to reduction in visible region, the increment of broad absorption in NIR region was detected, indicating the formation of polaron and bipolaron. At approximately −0.45 V, the visible absorption approaches its fully oxidized state and beyond this potential, minimal changes of entire spectra are observed. Full oxidized state was maintained at the potential of −0.75 V, having a transmissive sky blue color.

To evaluate the luminance changes on redox process, three of the conjugated copolymer films from BLD125 with varying absorbance were prepared to colorimetric analysis.

Figure 8:
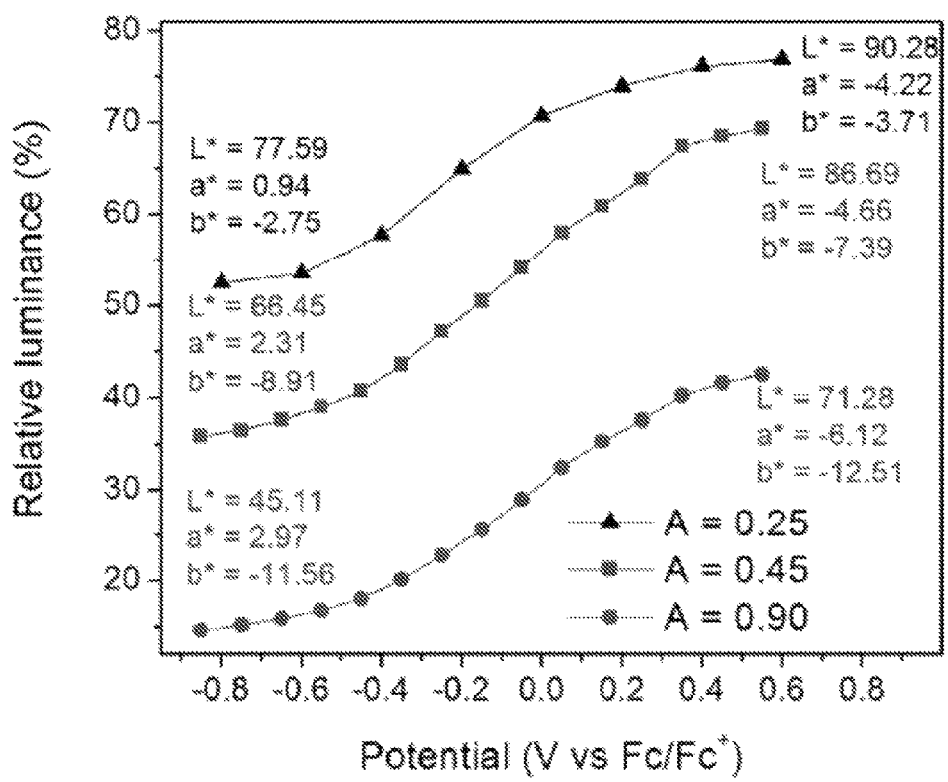
FIG. 8. illustrates the relative luminance as a function of applied potential and L*a*b* of the conjugated copolymer from BLD125 with varying absorbance.

As shown in FIG. 8, the conjugated copolymer films exhibit relative luminance change as high as 33.46 and low as 24.4. The highest relative luminance change was observed to the film of absorbance values of 0.45 at neutral. The neutral conjugated copolymer films exhibit L* value from 45.11 for the absorbance value of 0.90 to 77.59 for that of 0.25. Moreover, the films at neutral state reveal a dark black color with a* and b* values as low as 0.94 and −2.75. This violet hue is also observed by the spectrum transmitted by the conjugated copolymer film. The violet color is pale in the conjugated copolymer film, since violet hue is the least perceived by human eye compared to other hues. L* values of oxidized conjugated copolymer films vary from 71.28 to 90.28 with negative values of a* and b*, indicating sky blue color state as defined by the color spacer. This result clarifies the conjugated copolymer film of absorbance of 0.45 at neutral state exhibits the highest relative luminance change. Since oxidized state of the conjugated copolymer film are colored as defined by color space, considering the L*a*b* values of both neutral and oxidized states can result in the maximum relative luminance change.

Figure 9:
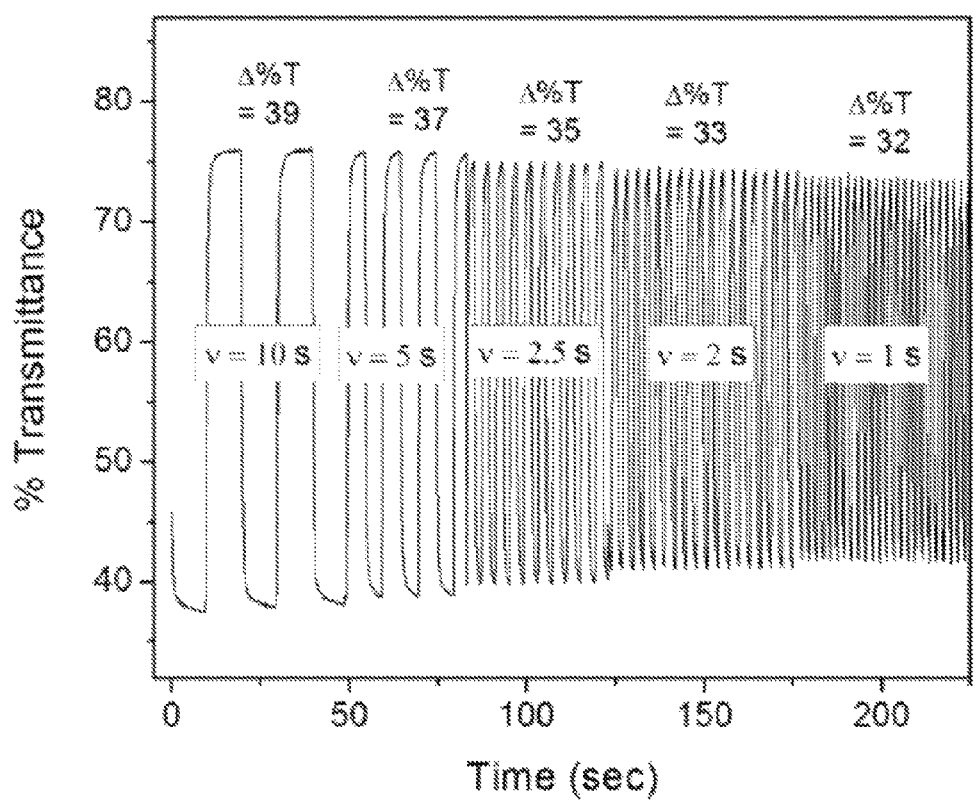
FIG. 9. illustrates the square-wave potential step absorptiometry of the conjugated copolymer from BLD125 on ITO in 0.1 M TBAPF$_6$/ACN electrolyte; % transmittance of the function of time at 500 nm of the conjugated copolymer from BLD125 with absorbance of 0.45; step times and % transmittance change are noted on the figure.

The switching response of electrochromic materials while changing color states is important in many applications. The response time of the same conjugated copolymer film of absorbance value of 0.45 was investigated examined by monitoring the % transmittance at the wavelength of maximum absorption change at 500 nm as a function of time by applying square-wave potential steps ranging from 10 to 1 s. A % transmittance change as high as 39% was recorded for the switching time of 10 s, and decreasing the time to 1 s results in 32% (see FIG. 9). The variation in contrast based on % transmittance of 7% was observed as the switch time is increased from 10 to 1 second.

Example 4. Preparation of a Flexible Electrochromic Device

A window type electrochromic device was prepared by spray coating BLD125 on an ITO-coated PET substrate and subsequently converted to a conjugated copolymer. The converted conjugated copolymer film on flexible PET was utilized the actively switching material. This working electrode was put together with another ITO-coated PET as counter electrode with polyelectrolyte sandwiched in between. The device was cured by exposing to UV, and tested for switching. A nearly perfect black color was observed at neutral state by applying the potential of −2 V. Conversely when the copolymer is oxidized at a device cell potential of 1 V, the device exhibits a sky blue color.

Experimental: Acetonitrile (ACN) and dichloromethane (DCM) were purchased from Fisher Scientific and distilled over calcium hydride ($CaH_2$) under nitrogen atmosphere. Silver nitrate, silver wire, ferrocene, and chloroform were purchased from Fisher Scientific and used as received. Tetra-n-butylammonium hexafluorophosphate ($TBAPF_6$), lithium trifluoromethane sulfonate (LITRIF), propylene carbonate (PC), polyethylene glycol diacrylate (PEG-DA), and dimethoxyphenylacetophenone (DMPAP) were purchased from Aldrich and used as received. PRE-BEDOT and PRE-BEBTD were synthesized according to Example 1. EDOT was purchased from Aldrich and distilled prior to use. ProDOT-$Me_2$ was synthesized according to the literature. BEBTD and BPBTD were synthesized according to the literature with modification. Indium-doped tin oxide (ITO)—coated glass (dimensions 7 mm×50 mm×0.7 mm, $R_s$=15-25Ω, unpolished float glass $SiO_2$ passivated) was purchased from Delta Technologies and cleaned by sonication in acetone prior to use. ITO-coated polyethylene terephthalate (PET) substrates were purchased from CP Films and cleaned by sonication in acetone prior to use. Copper tape was purchased from Newark and UV-sealant glue was purchased from Norland Optics. 50 to 100 μm glass beads were purchased from Polysciences and used as received. A CH Instruments 400 and 660a potentiostat were used for electrochemical study. Optical properties were measured by Varian Cary 5000 UV-vis-NIR spectrophotometer with a 150 mm DRA Integrating Sphere and corresponding Color software. Color data were calculated using a 10 degree standard observer angle, a measurement range of 360-860 nm in 1 nm intervals, and a D65 illuminant. A film of blend of siloxane precursors was prepared by using an Iwata spray coater.

A gel electrolyte was prepared from an electrolyte solution comprised of 3.0 g propylene carbonate, 7.0 g PEG-DA, 1.0 g LITRIF, 17.5 mg DMPAP was sonicated until a clear homogenous solution is obtained and then 5.0 mg glass beads were added. The ITO-coated PET substrates were spray coated with BLD125 from a chloroform solution using an Iwata spray coater and dried at 80° C. under nitrogen atmosphere for 10 min. The BLD125 was converted to conjugated copolymer in an 0.1 M $TBAPF_6$/ACN electrolyte bath by applying potential of 0.5 V vs. Fc/Fc+ for 10 seconds. Prior to device assembly, the conjugated copolymer from BLD125 films was washed with ACN and dried at air. The gel electrolyte solution described above was poured over the conjugated copolymer from BLD125 coated PET substrate, and another ITO PET substrate was placed on top of the gel electrolyte solution such that the ITO sides face one another. The glass beads maintained an even distance between two ITO electrodes and thereby prevented the shorting of the two ITO substrates. The sides of the device were then sealed using UV adhesive. A 365 nm UV light compartment was used to cure the gel electrolyte and UV adhesive.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All ranges disclosed herein are inclusive and combinable. The term "or" means "and/or."

Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The essential characteristics of the present invention are described completely in the foregoing disclosure. One skilled in the art can understand the invention and make various modifications without departing from the basic spirit of the invention, and without deviating from the scope and equivalents of the claims, which follow. Moreover, any combination of the above-described elements in all possible variations thereof is encompassed by the invention unless otherwise indicated herein or otherwise clearly contradicted by context.

What is claimed is:

1. A precursor mixture comprising:
two precursors,
wherein a first precursor is

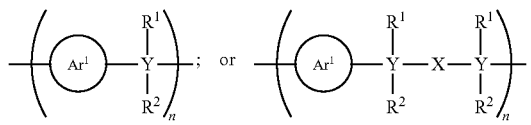

wherein $Ar^1$ is a heteroaryl electron donor unit; each occurrence of $R^1$ and $R^2$ is independently $C_3$-$C_{12}$ alkyl, $C_3$-$C_{122}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater; and
wherein a second precursor is

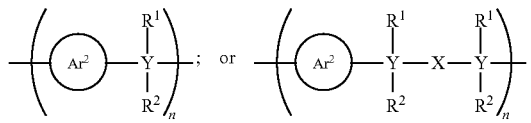

wherein $Ar^2$ is a heteroaryl electron acceptor unit that is bis-(3,4-(2',2'-dimethylpropylenedioxy)thiophene)-2,1,3-benzothiadiazole, imidazole, triazine, tetrazine, quinoline, pyridine, thiadiazole, or derivatives thereof; each occurrence of $R^1$ and $R^2$ is independently $C_3$-$C_{12}$ alkyl, $C_3$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater.

2. The precursor mixture of claim 1, wherein $Ar^1$ is 3,4-ethylenedioxythiophene, bis-3,4-ethylenedioxythiophene, thiophene, furan, pyrrole, indole, or derivatives thereof; and $Ar^2$ is bis-(3,4-(2',2'-dimethylpropylenedioxy)thiophene)-2,1,3-benzothiadiazole, imidazole, triazine, tetrazine, quinoline, pyridine, thiadiazole, or derivatives thereof.

3. The precursor mixture of claim 1, wherein Y is Si and X is O.

4. The precursor mixture of claim 1, wherein $R^1$ and $R^2$ are independently n-propyl, isopropyl, n-butyl, t-butyl, n-pentyl, 3-methylbutyl, sec-pentyl, cyclopentyl, cyclohexyl, n-hexyl, n-heptyl, n-septyl, n-octyl, or the perfluorinated groups thereof.

5. The precursor mixture of claim 1, wherein $R^1$ and $R^2$ are independently n-butyl, t-butyl, n-pentyl, 3-methylbutyl, sec-pentyl, cyclopentyl, cyclohexyl, n-hexyl, n-heptyl, n-septyl, n-octyl, or the perfluorinated groups thereof.

6. The precursor mixture of claim 1, wherein when converted by oxidative reaction process results in a conjugated copolymer exhibiting a black color.

7. A method of preparing a conductive copolymer film, comprising:
coating a substrate with a precursor mixture according to claim 1; and
converting the precursor mixture to a conductive conjugated copolymer;
wherein the coating is prepared by any one of the following processes: compression molding, melt coating, ink jet printing, screen printing, roll to roll printing processes, spin coating, meniscus and dip coating, spray coating, brush coating, spray casting, doctor blade application, or curtain casting.

8. A conjugated copolymer comprising a copolymer prepared by converting a precursor mixture comprising two precursors to the conjugated copolymer,
wherein the first precursor is

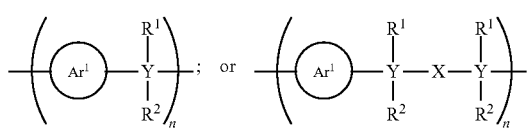

wherein $Ar^1$ is a heteroaryl electron donor unit; each occurrence of $R^1$ and $R^2$ is independently $C_3$-$C_{12}$ alkyl, $C_3$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater; and
wherein the second precursor is

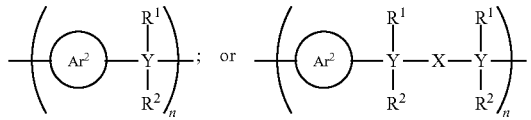

wherein $Ar^2$ is a heteroaryl electron acceptor unit that is bis-(3,4-(2',2'-dimethylpropylenedioxy)thiophene)-2,1,3-benzothiadiazole, imidazole, triazine, tetrazine, quinoline, pyridine, thiadiazole, or derivatives thereof; each occurrence of $R^1$ and $R^2$ is independently $C_3$-$C_{12}$ alkyl, $C_3$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater,
wherein the conjugated copolymer comprises a unit of $YR^1R^2$.

9. The conjugated copolymer of claim 8, wherein $Ar^1$ is 3,4-ethylenedioxythiophene, bis-3,4-ethylenedioxythiophene, thiophene, furan, pyrrole, indole, or derivatives thereof; and $Ar^2$ is bis-(3,4-(2',2'-dimethylpropylenedioxy)thiophene)-2,1,3-benzothiadiazole, imidazole, triazine, tetrazine, quinoline, pyridine, thiadiazole, or derivatives thereof.

10. The conjugated copolymer of claim 8, wherein Y is Si and X is O.

11. The conjugated copolymer of claim 8, wherein $R^1$ and $R^2$ are independently n-propyl, isopropyl, n-butyl, t-butyl, n-pentyl, 3-methylbutyl, sec-pentyl, cyclopentyl, cyclohexyl, n-hexyl, n-heptyl, n-septyl, n-octyl, or the perfluorinated groups thereof.

12. The conjugated copolymer of claim 8, wherein $R^1$ and $R^2$ are independently n-butyl, t-butyl, n-pentyl, 3-methylbutyl, sec-pentyl, cyclopentyl, cyclohexyl, n-hexyl, n-heptyl, n-septyl, n-octyl, or the perfluorinated groups thereof.

13. The conjugated copolymer of claim 8, wherein the conversion is by an oxidative reaction process.

14. The conjugated copolymer of claim 8, wherein the conjugated copolymer exhibits a black color.

15. An article prepared comprising the conductive conjugated copolymer of claim 8.

16. A conjugated copolymer comprising a copolymer prepared by converting a precursor mixture comprising two precursors to the conjugated copolymer,
wherein the first precursor is

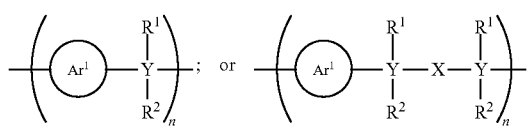

wherein $Ar^1$ is bis-3,4-ethylenedioxythiophene; each occurrence of $R^1$ and $R^2$ is independently $C_3$-$C_{12}$ alkyl, $C_3$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater; and
wherein the second precursor is

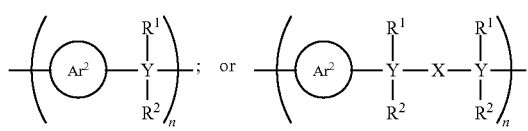

wherein $Ar^1$ is bis-(3,4-ethylenedioxythiophene)-2,1,3-benzothiadiazole; each occurrence of $R^1$ and $R^2$ is independently $C_3$-$C_{12}$ alkyl, $C_3$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater,
wherein the conjugated copolymer comprises a unit of $YR^1R^2$.

17. The conjugated copolymer of claim 16, wherein Y is Si and X is O.

18. An article prepared comprising the conductive conjugated copolymer of claim 16.

19. A method of preparing a conductive conjugated copolymer, comprising:
converting a precursor mixture comprising two precursors to the conductive conjugated copolymer,
wherein a first precursor is

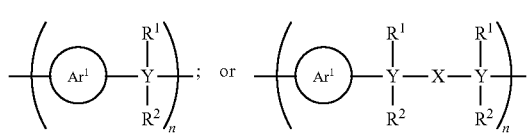

wherein $Ar^1$ is a heteroaryl electron donor unit; each occurrence of $R^1$ and $R^2$ is independently $C_3$-$C_{12}$ alkyl, $C_3$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater; and
wherein a second precursor is

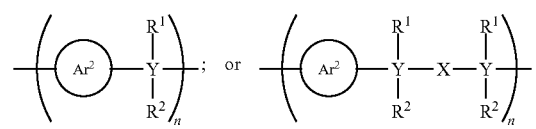

wherein $Ar^2$ is a heteroaryl electron acceptor unit that is bis-(3,4-ethylenedioxythiophene)-2,1,3-benzothiadiazole, bis-(3,4-(2',2'-dimethylpropylenedioxy)thiophene)-2,1,3-benzothiadiazole, imidazole, triazine, tetrazine, quinoline, pyridine, thiadiazole, or derivatives thereof with the proviso that when $Ar^2$ is bis-(3,4-ethylenedioxythiophene)-2,1,3-benzothiadiazole then $Ar^1$ is bis-3,4-ethylenedioxythiophene; each occurrence of $R^1$ and $R^2$ is independently $C_3$-$C_{12}$ alkyl, $C_3$-$C_{12}$ haloalkyl, or aryl; X is O, S, $(YR^1R^2)_x$, or $(CR^aR^b)_x$ wherein x is 0, 1, 2, 3, or 4, and $R^a$ and $R^b$ are independently hydrogen, $C_1$-$C_{12}$ alkyl, or $C_1$-$C_{12}$ haloalkyl; each occurrence of Y is independently Si, Ge, Sn, or Pb; and n is about 10 or greater,
wherein the conjugated copolymer comprises a unit of $YR^1R^2$.

20. The method of claim 19, wherein the converting is via chemical oxidation, electrochemical oxidation, or bromine conversion.

21. The method of claim 20, wherein the oxidative conversion occurs in solid state.

22. The method of claim 19, wherein $Ar^1$ is 3,4-ethylenedioxythiophene, bis-3,4-ethylenedioxythiophene, thiophene, furan, pyrrole, indole, or derivatives thereof; and $Ar^1$ is bis-(3,4-(2',2'-dimethylpropylenedioxy)thiophene)-2,1,3-benzothiadiazole, imidazole, triazine, tetrazine, quinoline, pyridine, thiadiazole, or derivatives thereof.

23. The method of claim 19, wherein Y is Si and X is O.

24. The method of claim 19, wherein $R^1$ and $R^2$ are independently n-propyl, isopropyl, n-butyl, t-butyl, n-pentyl, 3-methylbutyl, sec-pentyl, cyclopentyl, cyclohexyl, n-hexyl, n-heptyl, n-septyl, n-octyl, or the perfluorinated groups thereof.

25. The method of claim 19, wherein $R^1$ and $R^2$ are independently n-butyl, t-butyl, n-pentyl, 3-methylbutyl, sec-pentyl, cyclopentyl, cyclohexyl, n-hexyl, n-heptyl, n-septyl, n-octyl, or the perfluorinated groups thereof.

26. The method of claim 19, wherein the conjugated copolymer exhibits a black color.

* * * * *